US012626824B2

(12) United States Patent
Liu et al.

(10) Patent No.: US 12,626,824 B2
(45) Date of Patent: May 12, 2026

(54) METHOD AND SYSTEM OF MOLECULAR TYPING AND SUBTYING CLASSIFIER FOR IMMUNE-RELATED DISEASES

(71) Applicant: HUASHAN HOSPITAL, FUDAN UNIVERSITY, Shanghai (CN)

(72) Inventors: Jie Liu, Shanghai (CN); Feifei Luo, Shanghai (CN); Shaocong Mo, Shanghai (CN); Huan Song, Shanghai (CN)

(73) Assignee: HUASHAN HOSPITAL, FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 18/705,594

(22) PCT Filed: Aug. 12, 2022

(86) PCT No.: PCT/CN2022/112157
§ 371 (c)(1),
(2) Date: Apr. 29, 2024

(87) PCT Pub. No.: WO2023/071406
PCT Pub. Date: May 4, 2023

(65) Prior Publication Data
US 2024/0428955 A1 Dec. 26, 2024

(30) Foreign Application Priority Data
Oct. 29, 2021 (CN) .......................... 202111276527.X

(51) Int. Cl.
G16H 50/70 (2018.01)
G06N 20/10 (2019.01)
G16B 40/30 (2019.01)

(52) U.S. Cl.
CPC ............. G16H 50/70 (2018.01); G16B 40/30 (2019.02); G06N 20/10 (2019.01)

(58) Field of Classification Search
CPC ........ G16B 40/30; G16B 40/00; G06N 20/10; G16H 50/70
See application file for complete search history.

(56) References Cited

FOREIGN PATENT DOCUMENTS

CN 110993099 A 4/2020
CN 111369573 A 7/2020
(Continued)

OTHER PUBLICATIONS

Franks, Jennifer M., et al. "A machine learning classifier for assigning individual patients with systemic sclerosis to intrinsic molecular subsets." Arthritis & rheumatology 71.10 (2019): 1701-1710. (Year: 2019).*

(Continued)

*Primary Examiner* — Anna Skibinsky
*Assistant Examiner* — Guozhen Liu
(74) *Attorney, Agent, or Firm* — Bayramoglu Law Offices LLC

(57) ABSTRACT

A method and a system of molecular typing and subtyping classifier for immune-related diseases are provided. The method includes: conducting molecular typing via a clustering algorithm in a training set to obtain a plurality of subtypes stably appearing in the training set and a marker gene for each subtype; conducting enrichment analysis on marker genes for the plurality of subtypes, conducting immune cell infiltration evaluation on the plurality of subtypes, and dividing the plurality of subtypes into a plurality of subtype classes according to results of the analysis and the evaluation; comparing treatment response rates of different subtype classes through a comparison set to determine a subtype class to be identified; constructing a support vector machine model with feature genes screened and an optimal (Continued)

Acquire an immune-related disease chip dataset and divide the immune-related disease chip dataset into a training set, a validation set, and a comparison set Conduct molecular typing via a clustering algorithm in the training set to obtain a plurality of subtypes stably appearing in the training set and a marker gene for each subtype, and verify a stability of molecular typing results through the validation set Conduct enrichment analysis on marker genes for the plurality of subtypes, conduct immune cell infiltration evaluation on the plurality of subtypes, and divide the plurality of subtypes into a plurality of subtype classes according to results of the enrichment analysis and the immune cell infiltration evaluation Compare treatment response rates of different subtype classes through the comparison set to determine a subtype class to be identified Construct a support vector machine model with characteristic genes selected from the marker genes and an optimal parameter combination for a support vector machine Input immune-related disease data to be classified into the support vector machine model to determine whether the immune-related disease data to be classified is the subtype class to be identified parameter combination; and determining whether immune-related disease data to be classified is the subtype class to be identified.

5 Claims, 23 Drawing Sheets

(56)                    References Cited

FOREIGN PATENT DOCUMENTS

| CN | 111739584 A | 10/2020 |
| CN | 112116957 A | 12/2020 |
| CN | 113096730 A | 7/2021 |
| CN | 113903400 A | 1/2022 |
| WO | 2019108695 A1 | 6/2019 |

OTHER PUBLICATIONS

Keerthikumar, S. H. I. V. A. K. U. M. A. R., et al. "Prediction of candidate primary immunodeficiency disease genes using a support vector machine learning approach." DNA research 16.6 (2009): 345-351. (Year: 2009).*

Pinal-Fernandez, Iago, et al. "Machine learning algorithms reveal unique gene expression profiles in muscle biopsies from patients with different types of myositis." Annals of the rheumatic diseases 79.9 (2020): 1234-1242. (Year: 2020).*

Stankovic, Biljana, et al. "Machine learning modeling from omics data as prospective tool for improvement of inflammatory bowel disease diagnosis and clinical classifications." Genes 12.9 (2021): 1438. (Year: 2021).*

Zhao, Qi, et al. "CrossICC: iterative consensus clustering of cross-platform gene expression data without adjusting batch effect." Briefings in Bioinformatics 21.5 (2020): 1818-1824. (Year: 2020).*

He, Manrong, et al. "Machine learning gene expression predicting model for ustekinumab response in patients with Crohn's disease ." Immunity, inflammation and disease 9.4 (2021): 1529-1540. (Year: 2021).*

Däbritz, Jan. "Granulocyte macrophage colony-stimulating factor and the intestinal innate immune cell homeostasis in Crohn's disease." American Journal of Physiology-Gastrointestinal and Liver Physiology 306.6 (2014): G455-G465. (Year: 2014).*

Yu, Bing, et al. "Diagnostic and predictive value of immune-related genes in Crohn's disease." Frontiers in Immunology 12 (2021): 643036. (Year: 2021).*

Khorasani, Hanieh Marvi, Hamid Usefi, and Lourdes Pena-Castillo. "Detecting ulcerative colitis from colon samples using efficient feature selection and machine learning." Scientific reports 10.1 (2020): 13744. (Year: 2020).*

Li Hui, et al., Study of Tumor Molecular Prediction Model Based on Gene Expression Profiles, Acta Electronica Sinica, 2008, pp. 989-992, vol. 36 No.5.

* cited by examiner

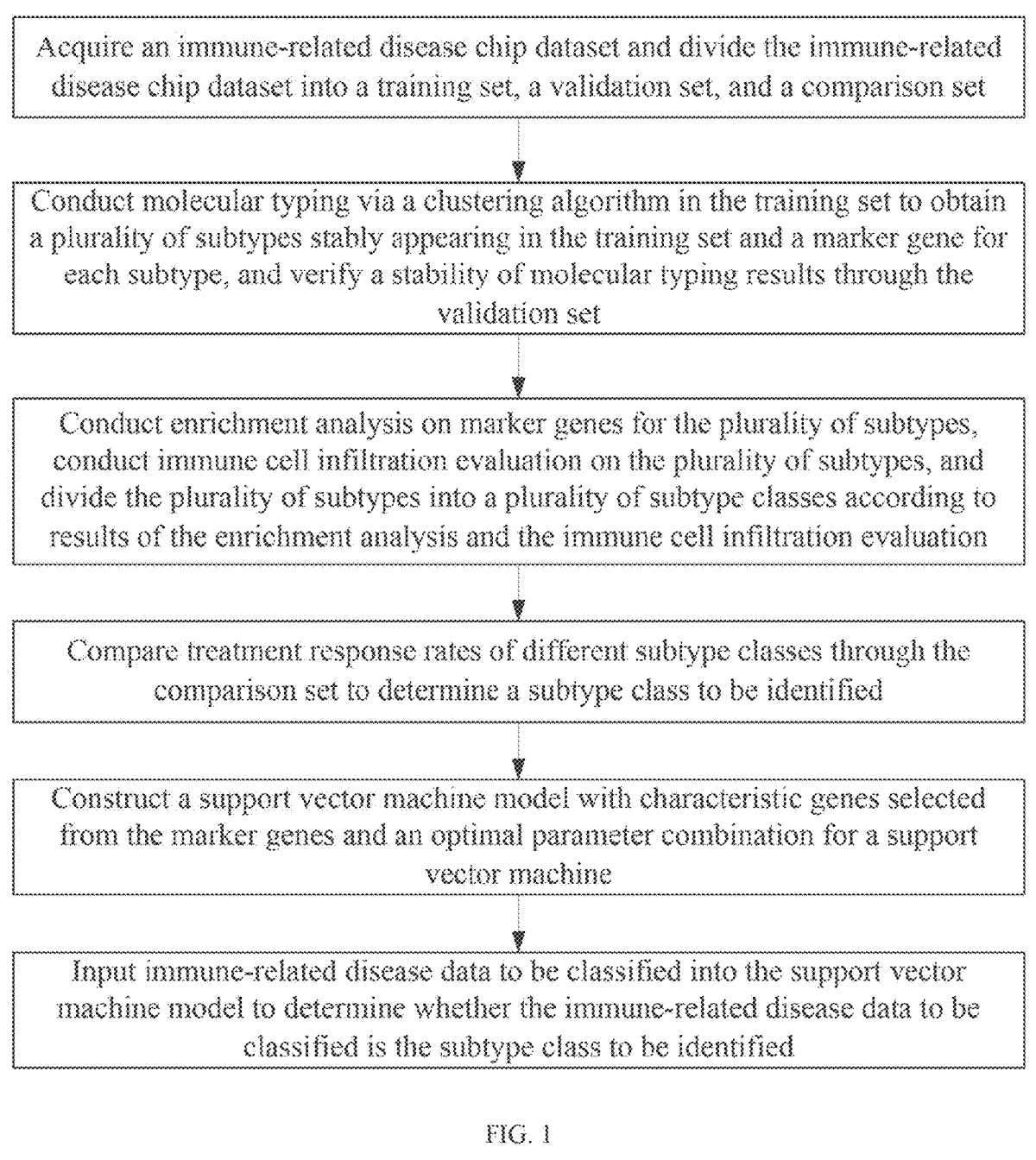

Acquire an immune-related disease chip dataset and divide the immune-related disease chip dataset into a training set, a validation set, and a comparison set Conduct molecular typing via a clustering algorithm in the training set to obtain a plurality of subtypes stably appearing in the training set and a marker gene for each subtype, and verify a stability of molecular typing results through the validation set Conduct enrichment analysis on marker genes for the plurality of subtypes, conduct immune cell infiltration evaluation on the plurality of subtypes, and divide the plurality of subtypes into a plurality of subtype classes according to results of the enrichment analysis and the immune cell infiltration evaluation Compare treatment response rates of different subtype classes through the comparison set to determine a subtype class to be identified Construct a support vector machine model with characteristic genes selected from the marker genes and an optimal parameter combination for a support vector machine Input immune-related disease data to be classified into the support vector machine model to determine whether the immune-related disease data to be classified is the subtype class to be identified

FIG. 1

GSE87466

GSE107499

GSE75214

GSE83687

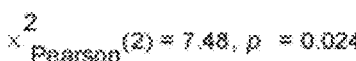
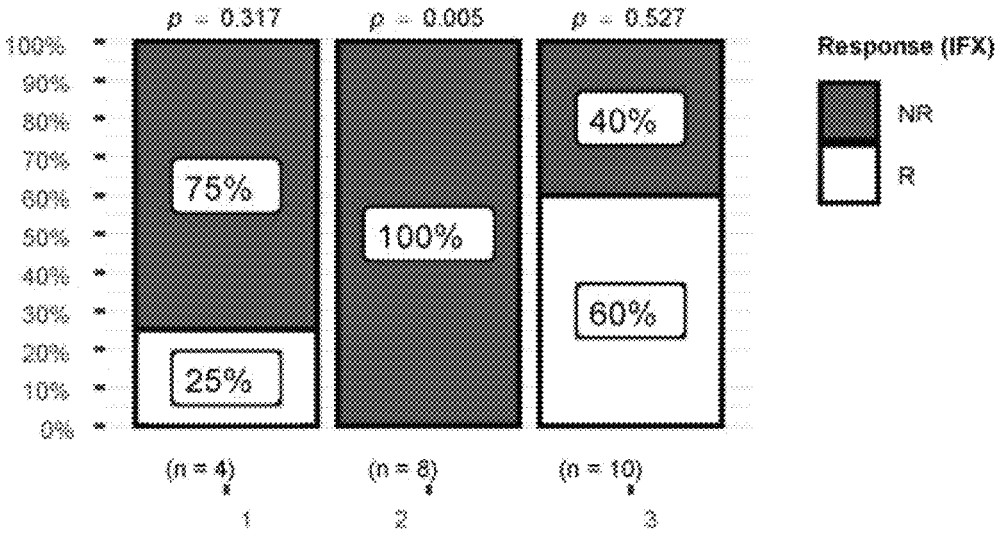
FIG. 4G
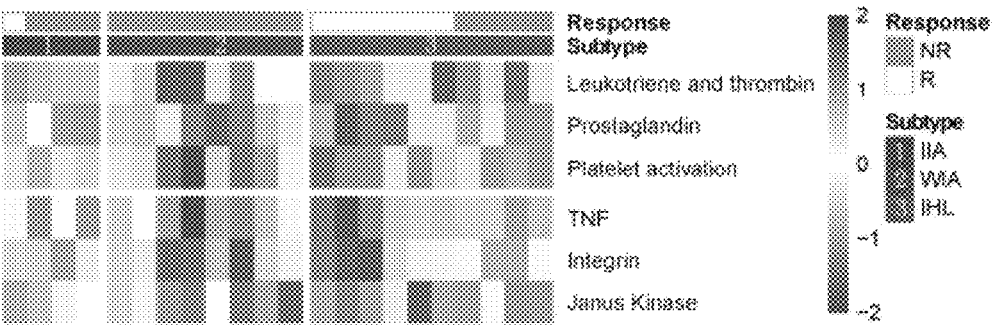
FIG. 4H

GSE112366

GSE75214

GSE179285

GSE100833

FIG. 6E

METHOD AND SYSTEM OF MOLECULAR TYPING AND SUBTYING CLASSIFIER FOR IMMUNE-RELATED DISEASES

CROSS REFERENCE TO THE RELATED APPLICATIONS

This application is the national phase entry of International Application No. PCT/CN2022/112157, filed on Aug. 12, 2022, which is based upon and claims priority to Chinese Patent Application No. 202111276527.3, filed on Oct. 29, 2021, the entire contents of which are incorporated herein by reference.

TECHNICAL FIELD

The present disclosure relates to the technical field of precision medicine, and specifically to a method and a system of molecular typing and subtyping classifier for immune-related diseases based on machine learning of artificial intelligence.

BACKGROUND

Immune-related diseases are caused by an imbalance in the immune regulation of an organism. There are many treatments for immune-related diseases, and in particular, biological agents such as monoclonal antibodies are increasingly used. However, the prognoses of different patients with a same immune-related disease are not the same clinically, indicating that immune states of the different patients with the same disease have extensive heterogeneities and can hardly be distinguished according to clinical manifestations. Therefore, it is urgent to accurately type the immunocharacterization of a patient with an immune-related disease at a molecular level to facilitate the clinical prognosis and treatment.

For example, ulcerative colitis (UC), a typical immune-related disease, is characterized by a chronic inflammation from a rectum to a proximal colon, and brings a huge burden to the global medical care. Drugs for treating UC include 5-aminosalicylic acid (5-ASA) drugs, glucocorticoids, azathioprine, anti-tumor necrosis factor (TNF) drugs, anti-integrins, Janus kinase inhibitors, or the like. Currently, in clinical practice, the 5-ASA treatment is mainly adopted for mild patients and the glucocorticoids and anti-TNF drugs are often adopted for the remission treatment of moderate to severe patients, but the prognoses of patients are limited by drug resistance, adverse drug reactions, and high drug prices. From the perspective of treatment mechanisms, the disruption of intestinal homeostasis, the dysfunction of an intestinal barrier, and an inflammatory response are pathological characteristics of UC patients. A balance between negative regulators for inflammation and pro-inflammatory factors in an intestinal epithelium of a UC patient is disrupted, and the activation of neutrophils and lymphocytes and various cytokines such as interleukin-9 (IL-9), interleukin-13 (IL-13), interleukin-23 (IL-23), and interleukin-36 (IL-36) are involved in an intestinal inflammation of a UC patient. It can be concluded that the disruption of intestinal immune homeostasis is the essence of UC onset, indicating that poor medication effects for some UC patients are related to the heterogeneities of local immune infiltration of lesions.

Due to the lack of molecular typing for UC, the clinical medication for UC is mainly based on the severity of UC pathology. The patent document CN110993099A discloses a method and a system for evaluating the severity of UC based on deep learning, where a UC severity evaluation model is used to output score prediction results of vascular typing, spontaneous bleeding, and erosive ulcer characteristics under a Mayo endoscope, and then the score prediction results of vascular typing, spontaneous bleeding, and erosive ulcer characteristics are accumulated to obtain an activity index score of UC under the endoscope. In the prior art, according to a severity evaluation result, a single therapy solution or a combined therapy solution is adopted. For example, glucocorticoids and immunobiologic agents are often used for the remission treatment of moderate to severe patients. The glucocorticoids have broad-spectrum effects, but have large side effects. The immunobiologic agents often target specific immune targets, but have limited effects and high prices, resulting in a poor accuracy and a heavy economic burden.

In addition to UC, many immune-related diseases, such as Crohn's disease (CD), systemic lupus erythematosus, and rheumatoid arthritis, face the above clinical problems. The treatments of these diseases have one thing in common, which involves the use of drugs to dampen the autoimmune response directed against the body itself. The most common drugs are glucocorticoid such as prednisone, hydrocortisone, and dexamethasone. Immunosuppressive drugs have a major common adverse effect, that is, the drugs will affect the anti-infection and anti-tumor immune functions of a body to varying degrees.

Therefore, the molecular typing for immune-related diseases is of great significance for understanding the heterogeneities of diseases to allow personalized treatments and avoid over-treatments. However, according to the existing reports, there are few studies on the accurate and high-quality molecular typing for immune-related diseases. In the present disclosure, UC and CD are taken as two examples to illustrate a method and a system of molecular typing and subtyping classifier for immune-related diseases.

SUMMARY

In view of the defects in the prior art, an objective of the present disclosure is to provide a method and a system of molecular typing and subtyping classifier for immune-related diseases.

The method of molecular typing and subtyping classifier for immune-related diseases provided in the present disclosure includes:

a data acquisition step: acquiring an immune-related disease microarray dataset and dividing the immune-related disease microarray dataset into a training set, a validation set, and a comparison set;

a molecular typing step: conducting molecular typing via a clustering algorithm in the training set to obtain a plurality of subtypes stably appearing in the training set and a marker gene for each subtype, and verifying a stability of molecular typing results through the validation set;

an analysis and evaluation step: conducting enrichment analysis on marker genes for the plurality of subtypes, conducting immune cell infiltration evaluation on the plurality of subtypes, and dividing the plurality of subtypes into a plurality of subtype classes according to results of the enrichment analysis and the immune cell infiltration evaluation;

a comparison step: comparing treatment response rates of different subtype classes through the comparison set to determine a subtype class to be identified;

a classifier construction step: constructing a support vector machine model with feature genes selected from the marker genes and an optimal parameter combination for a support vector machine; and a classifying step: inputting immune-related disease data to be classified into the support vector machine model to determine whether the immune-related disease data to be classified is the subtype class to be identified.

Preferably, the immune-related disease microarray dataset is acquired from a GEO database, and the immune-related disease microarray dataset includes a UC microarray dataset or a CD microarray dataset;

corresponding to the UC microarray dataset, the training set includes GSE87466, GSE107499, and GSE75214, the validation set includes GSE83687 and GSE126124, and the comparison set includes GSE114527, GSE73661, and GSE16879; and corresponding to the CD microarray dataset, the training set includes GSE112366, GSE75214, GSE179285, and GSE100833, the validation set includes GSE16879, and the comparison set includes GSE112366.

Preferably, the clustering algorithm includes a CrossICC algorithm, the enrichment analysis adopts a clusterProfiler package, and the immune cell infiltration evaluation adopts CIBERSORT and ssGSEA; and the plurality of subtype classes include an immune activation class and an immune homeostasis class, or an innate immune activation (IIA) class, a whole immune activation (WIA) class, and an immune homeostasis like (IHL) class, or an IHL class, an IIA class, and an intermediate class, or an immune homeostasis class and classes other than the immune homeostasis class.

Preferably, a method for selecting the feature genes includes:

setting a maximum number of runs and a number of trees for marker genes of all subtypes by a random forest method in a Boruta package, and inputting marker genes left after screening into Lasso regression of 10-fold cross-validation to leave marker genes with non-zero parameters as the feature genes.

Preferably, the method further includes: conducting a prediction and an evaluation with the constructed support vector machine model in the training set and the validation set, and evaluating performance of classifying by a confusion matrix, where:

an accuracy=samples correctly classified/total samples;

a sensitivity=*a* number of positive samples correctly classified/*a* total number of positive samples;

a specificity=*a* number of negative samples correctly classified/*a* total number of negative samples;

a false positive rate=negative samples determined to *be* positive/*a* total number of negative samples; and a false negative rate=positive samples determined to *be* negative/*a* total number of positive samples.

Preferably, a gamma value and a cost value are selected based on the feature genes to obtain the optimal parameter combination.

The system of molecular typing and subtyping classifier for immune-related diseases provided in the present disclosure includes:

a data acquisition module configured to: acquire an immune-related disease microarray dataset and divide the immune-related disease microarray dataset into a training set, a validation set, and a comparison set;

a molecular typing module configured to: conduct molecular typing via a clustering algorithm in the training set to obtain a plurality of subtypes stably appearing in the training set and a marker gene for each subtype, and verify a stability of molecular typing results through the validation set;

an analysis and evaluation module configured to: conduct enrichment analysis on marker genes for the plurality of subtypes, conduct immune cell infiltration evaluation on the plurality of subtypes, and divide the plurality of subtypes into a plurality of subtype classes according to results of the enrichment analysis and the immune cell infiltration evaluation;

a comparison module configured to: compare treatment response rates of different subtype classes through the comparison set to determine a subtype class to be identified;

a classifier construction module configured to: construct a support vector machine model with feature genes selected from the marker genes and an optimal parameter combination for a support vector machine; and a classifying module configured to: input immune-related disease data to be classified into the support vector machine model to determine whether the immune-related disease data to be classified is the subtype class to be identified.

Preferably, the immune-related disease microarray dataset is acquired from a GEO database, and the immune-related disease microarray dataset includes a UC microarray dataset or a CD microarray dataset;

corresponding to the UC microarray dataset, the training set includes GSE87466, GSE107499, and GSE75214, the validation set includes GSE83687 and GSE126124, and the comparison set includes GSE114527, GSE73661, and GSE16879; and corresponding to the CD microarray dataset, the training set includes GSE112366, GSE75214, GSE179285, and GSE100833, the validation set includes GSE16879, and the comparison set includes GSE112366.

Preferably, the clustering algorithm includes a CrossICC algorithm, the enrichment analysis adopts a clusterProfiler package, and the immune cell infiltration evaluation adopts CIBERSORT and ssGSEA; and the plurality of subtype classes include an immune activation class and an immune homeostasis class, or an IIA class, a WIA class, and an IHL class, or an IHL class, an IIA class, and an intermediate class, or an immune homeostasis class and classes other than the immune homeostasis class.

Preferably, a method for selecting the feature genes includes:

setting a maximum number of runs and a number of trees for marker genes of all subtypes by a random forest method in a Boruta package, and inputting marker genes left after screening into Lasso regression of 10-fold cross-validation to leave marker genes with non-zero parameters as the feature genes.

Compared with the prior art, the present disclosure has the following beneficial effects:

A general process for the molecular typing of an immune-related disease in the present disclosure is as follows: clustering is conducted with CrossICC in a training set, subtypes are verified in a validation set and subjected to enrichment analysis and immune infiltration evaluation to obtain immune subtypes, and treatment response rates of subtypes are compared in a comparison set. This solution can be applied to the molecular typing of various immune-related diseases, and is not limited to the two diseases of UC and CD in the present disclosure.

In the present disclosure, the molecular subtyping of an immune-related disease can be allowed through large-scale clinical samples and machine learning, subtypes with stable characteristics can be accurately identified in clinical practice, and subtypes with optimal and preferable treatment response rates under different treatment modes can be determined by comparing treatment response rates of the subtypes, which is conducive to the subsequent accurate drug selection and economical treatment.

BRIEF DESCRIPTION OF THE DRAWINGS

FIG. 1 is a flow chart of the present disclosure;

FIG. 2A to FIG. 5B are accompanying drawings for a UC example, where:

FIG. 2A, FIG. 2B, and FIG. 2C are schematic diagrams of molecular subtypes obtained by training a CrossICC algorithm with three training sets, respectively;

FIG. 4G is a schematic diagram of response rates and statistical tests of an IFX therapy in GSE16879;

FIG. 4H is a schematic diagram of comparison of GSE16879 therapeutic targets among subtypes;

FIG. 5B is a schematic diagram of evaluating an accuracy of a classifier by a confusion matrix; and FIG. 6A to FIG. 9 are accompanying drawings for a CD example, where:

Figure 6E:
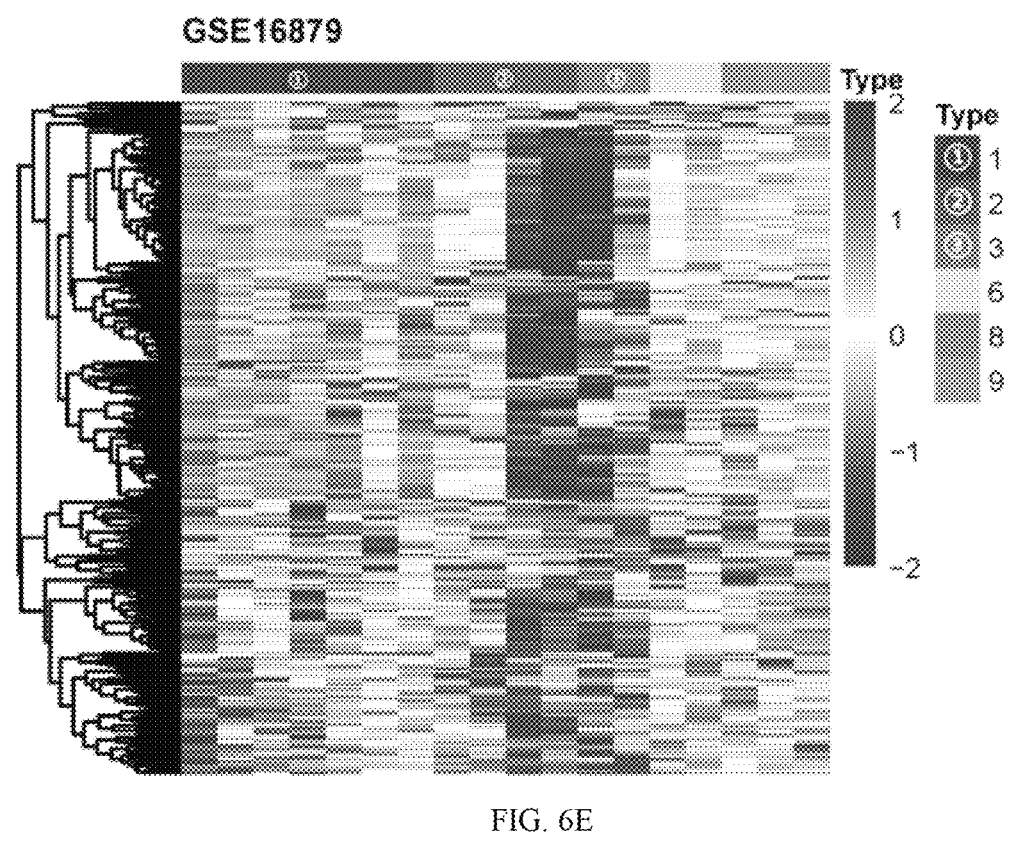

FIG. 6A, FIG. 6B, FIG. 6C, and FIG. 6D are schematic diagrams of molecular subtypes of CD obtained by training a CrossICC algorithm with four training sets, respectively;

FIG. 6E is a schematic diagram of molecular subtypes obtained by verifying a CrossICC algorithm with a validation set;

FIG. 9 is a schematic diagram of evaluating an accuracy of a classifier by a confusion matrix.

DETAILED DESCRIPTION OF THE EMBODIMENTS

Figure 2A:
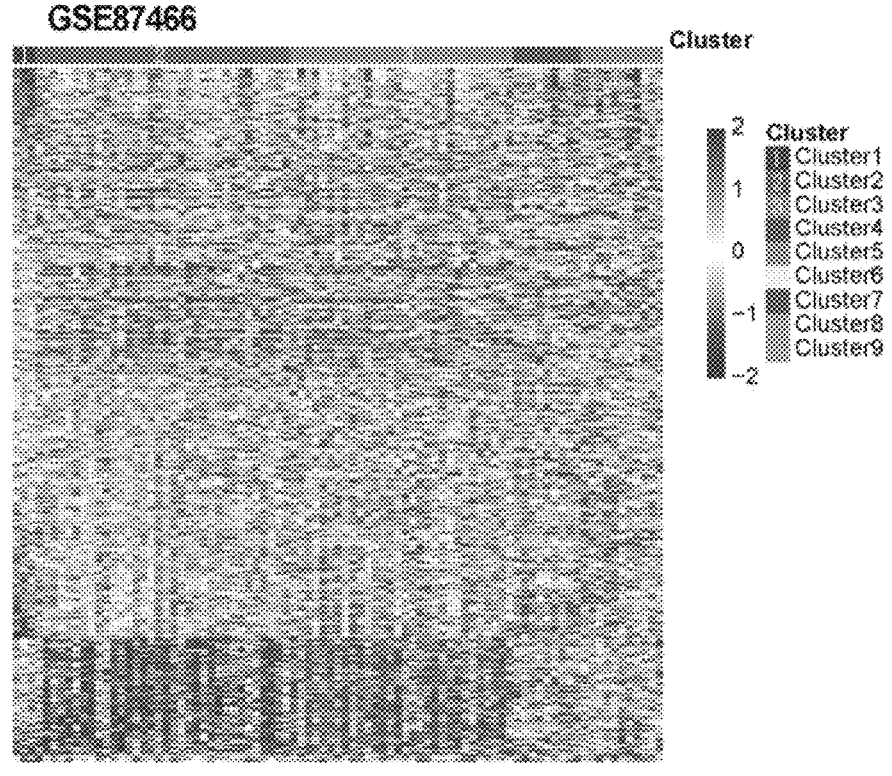

The present disclosure is described in detail below with reference to specific embodiments. The following embodiments will help those skilled in the art further understand the present disclosure, but will not limit the present disclosure in any way. It should be noted that several variations and improvements can also be made by a person of ordinary skill in the art without departing from the conception of the present disclosure. These all fall within the protection scope of the present disclosure.

As shown in FIG. 1, the present disclosure provides a method of molecular typing and subtyping classifier for immune-related diseases, including:

a data acquisition step: an immune-related disease microarray dataset is acquired and divided into a training set, a validation set, and a comparison set;

a molecular typing step: molecular typing is conducted via a clustering algorithm in the training set to obtain a plurality of subtypes stably appearing in the training set and a marker gene for each subtype, and a stability of molecular typing results is verified through the validation set;

an analysis and evaluation step: marker genes for the plurality of subtypes are subjected to enrichment analysis, the plurality of subtypes are subjected to immune cell infiltration evaluation, and the plurality of subtypes are divided into a plurality of subtype classes according to results of the enrichment analysis and the immune cell infiltration evaluation;

a comparison step: treatment response rates of different subtype classes are compared through the comparison set to determine a subtype class to be identified;

a classifier construction step: a support vector machine model is constructed with feature genes selected from the marker genes and an optimal parameter combination for a support vector machine; and a classifying step: immune-related disease data to be classified is input into the support vector machine model to determine whether the immune-related disease data to be classified is the subtype class to be identified.

Example 1: UC

In this example, a method of molecular typing and subtyping classifier for UC is provided, including:

A data acquisition step: A UC microarray dataset is acquired and divided into a training set, a validation set, and a comparison set. In the present disclosure, the UC microarray dataset is acquired from a GEO database, where GSE87466 (n=87). GSE107499 (n=47), and GSE75214 (n=74) are adopted as a training set, GSE83687 (n=28) and GSE126124 (n=18) are adopted as a typing validation set, and GSE114527 (n=15), GSE73661 (n=64), and GSE16879 (n=24) are adopted to compare treatment response rates. Only tissues from colons are included, and only mucosal tissues involved by active UC are included. In addition, normal samples are retained as a control group. A total of 208 mucosal tissues are included in the training set. Any data is transformed by log 2. A therapeutic target pathway gene set is downloaded from GSEA-Msigdb (http://www.gsea-msigdb.org/gsea/msigdb/).

A molecular typing step: Molecular typing is conducted via a clustering algorithm in the training set to obtain a plurality of subtypes stably appearing in the training set and a marker gene for each subtype, and a stability of typing training results is verified through the validation set. In the present disclosure, a CrossICC algorithm is used to conduct training with the training sets of GSE87466, GSE107499, and GSE75214 to obtain subtypes and a marker gene for each subtype. Typing results are predicted on the validation sets of GSE83687 and GSE126124, and whether the typing results are stable is observed. If a typing result is not stable, dataset selection and quality control are required once again for the training sets.

An analysis and evaluation step: Marker genes for the plurality of subtypes are subjected to enrichment analysis, the plurality of subtypes are subjected to immune cell infiltration evaluation, and the plurality of subtypes are divided into a plurality of different subtype classes according to results of the enrichment analysis and the immune cell infiltration evaluation. In the present disclosure, the marker gene for each subtype is subjected to enrichment analysis with a clusterProfiler package, and each subtype is subjected to immune cell infiltration evaluation with CIBERSORT and ssGSEA.

A comparison step: Treatment response rates of different subtype classes are compared through the comparison set. Response data of therapies including a glucocorticoid therapy and a biological agent therapy in GSE114527, GSE73661, and GSE16879 is downloaded, and only mucosal expression profile data before drug administration is used for subtype identification. If different subtype classes have different drug treatment effects, it can indicate a clinical value of the molecular typing of the present disclosure and the necessity for constructing a classifier for clinical practice.

A classifier construction step: A support vector machine model is constructed with feature genes selected from the marker genes and an optimal parameter combination for a support vector machine. According to results of CrossICC, samples are divided into the following two classes: an IHL class and subtypes other than the IHL class. Based on marker genes for all subtypes, a maximum number of runs is set to 100 and a number of trees is set to 500 by a random forest method in a Boruta package, and feature genes left after screening are input into Lasso regression of 10-fold cross-validation to leave genes with non-zero parameters as the final feature genes. The support vector machine method is used for subtype determination. Before each execution of the support vector machine, feature genes in each sample are normalized (scale) to avoid the influence of a feature gene with a too-large standard deviation on a support vector machine. After the support vector machine model is generated, a prediction and an evaluation are conducted in a training set and two external validation sets. The performance of classifying is evaluated by a confusion matrix, where:

an accuracy=samples correctly classified/total samples;

8 a sensitivity=a number of positive samples correctly classified/a total number of positive samples;

a specificity=a number of negative samples correctly classified/a total number of negative samples;

a false positive rate=negative samples determined to be positive/a total number of negative samples; and a false negative rate=positive samples determined to be negative/a total number of positive samples.

A statistical analysis step: A Wilcoxon test is used to compare means of two groups of continuous variables. A Kruskal-Wallis test is used to compare means of a plurality of groups of continuous variables. A chi-square test is adopted for classification variables. Any statistical analysis is conducted in R (version 4.0.3).

A classifying step: UC data to be classified is input into the support vector machine model to determine whether the UC data to be classified is an IHL class.

Figure 2B:
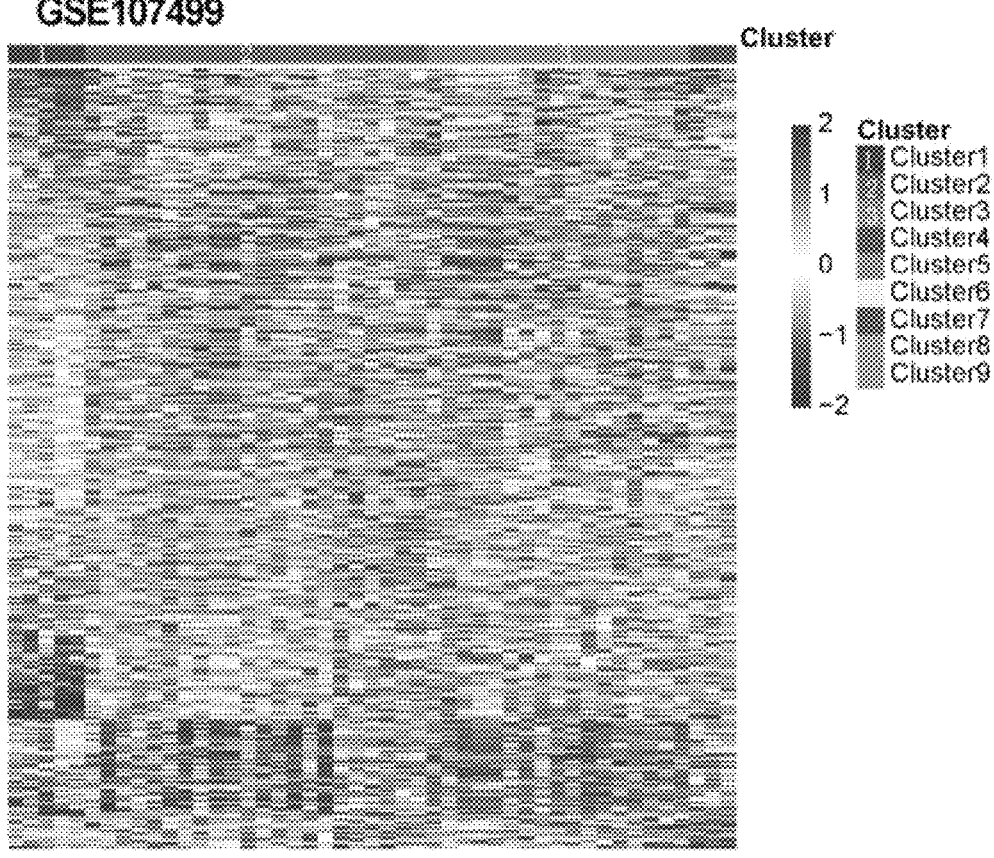
Figure 2C:
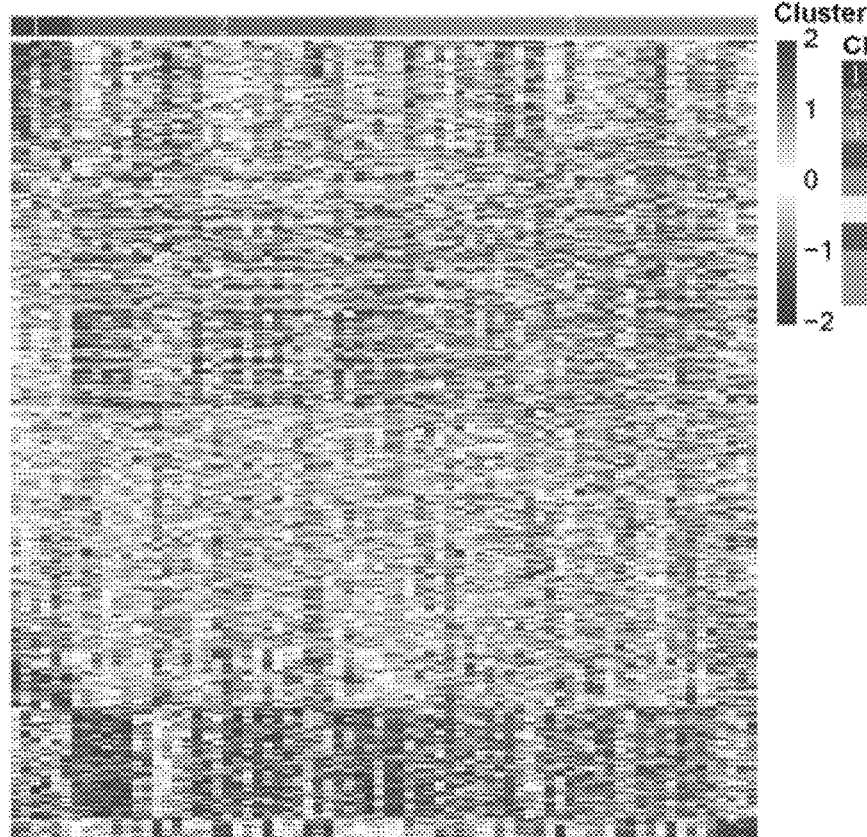
Figure 2D:
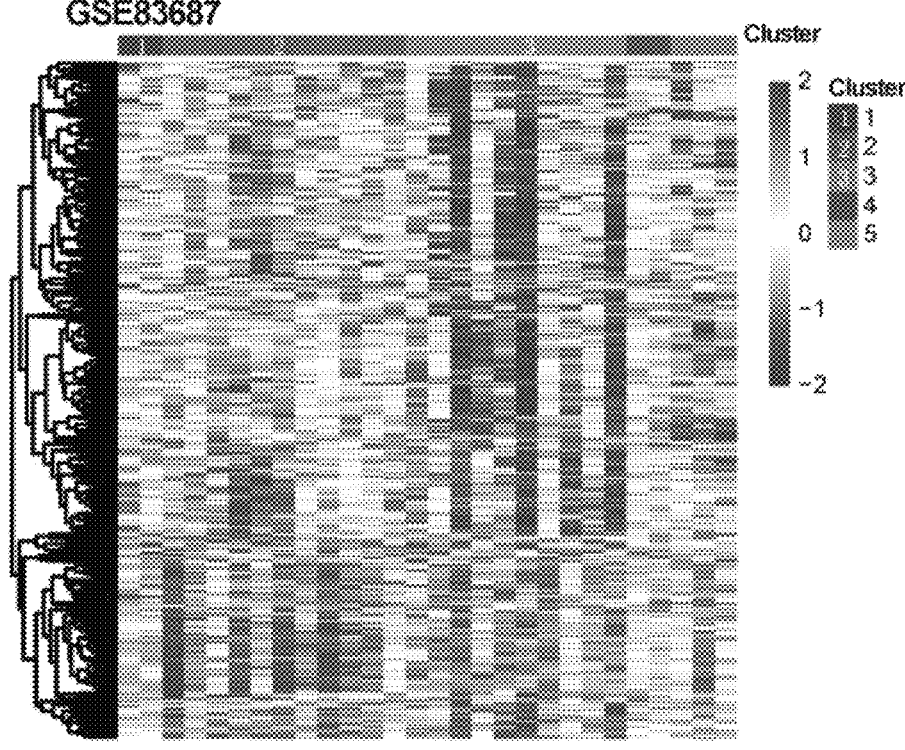
FIG. 2D and FIG. 2E are schematic diagrams of molecular subtypes of UC obtained by verifying a CrossICC algorithm with two validation sets, respectively.
Figure 2E:
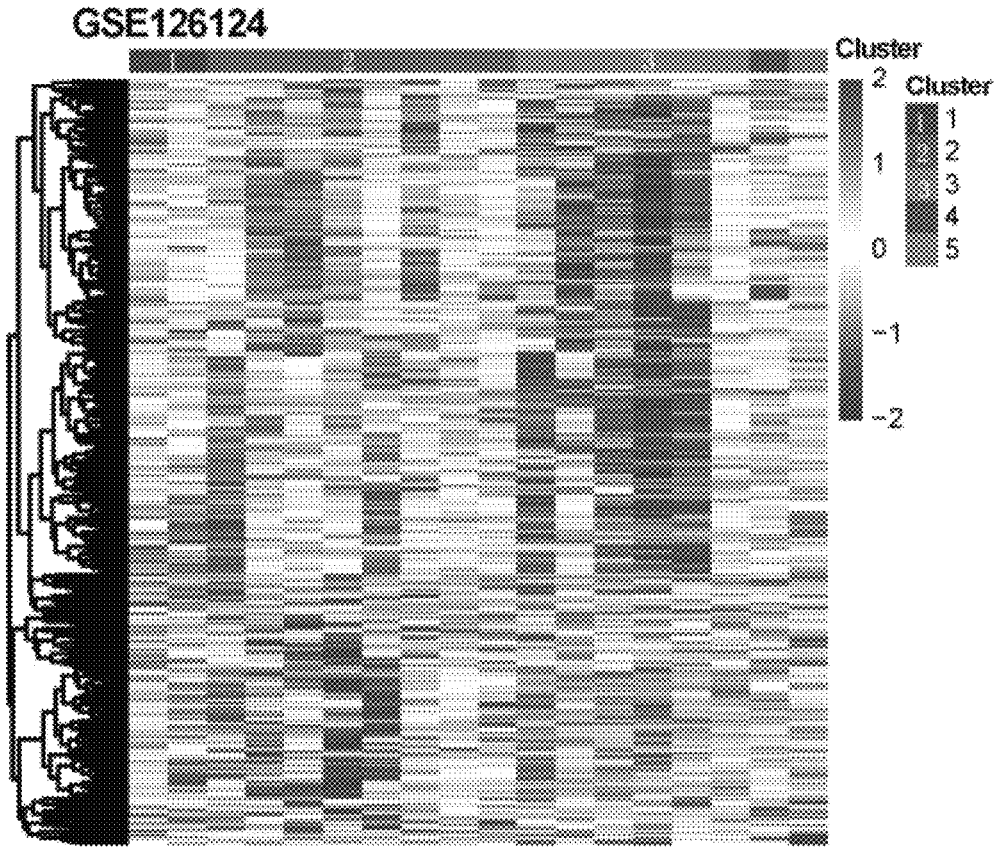

Experimental Results (1) Three Stable Molecular Subtypes of UC are Identified by CrossICC A series of subtypes are identified by the CrossICC algorithm in the three datasets of GSE87466, GSE107499, and GSE75214, where cluster 1, cluster 2, and cluster 3 stably appear in each dataset (FIGS. 2A-2C). A marker gene for each subtype is obtained. To confirm a stability of typing, the two external validation sets of GSE83687 and GSE126124 are used for subtype validation, and results show that subtypes of cluster 1, cluster 2, and cluster 3 are also available in these two datasets according to marker genes (FIGS. 2D-2E).

(2) Enrichment Analysis and Immune Infiltration of Subtypes

Figure 3A:
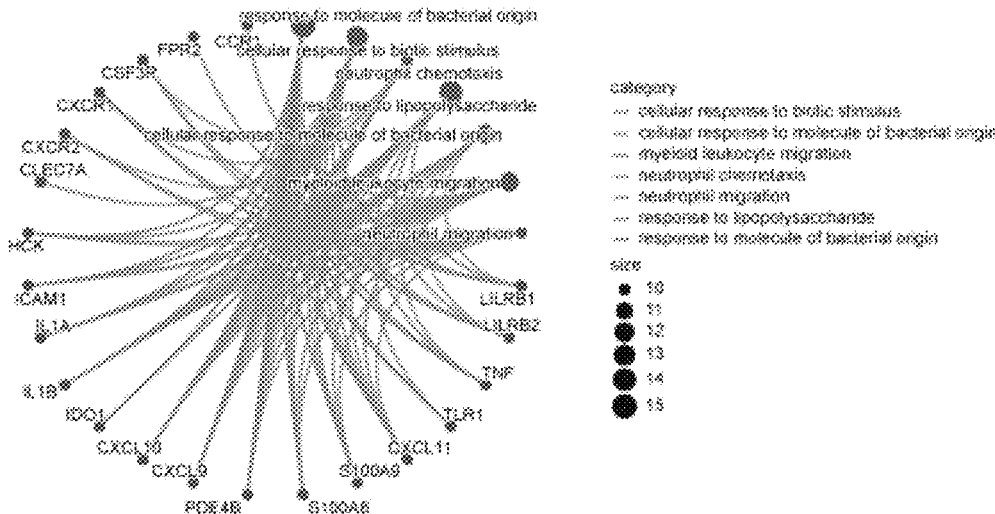
FIG. 3A, FIG. 3B, and FIG. 3C are schematic diagrams of results of GO enrichment analysis for three subtypes, respectively.
Figure 3B:
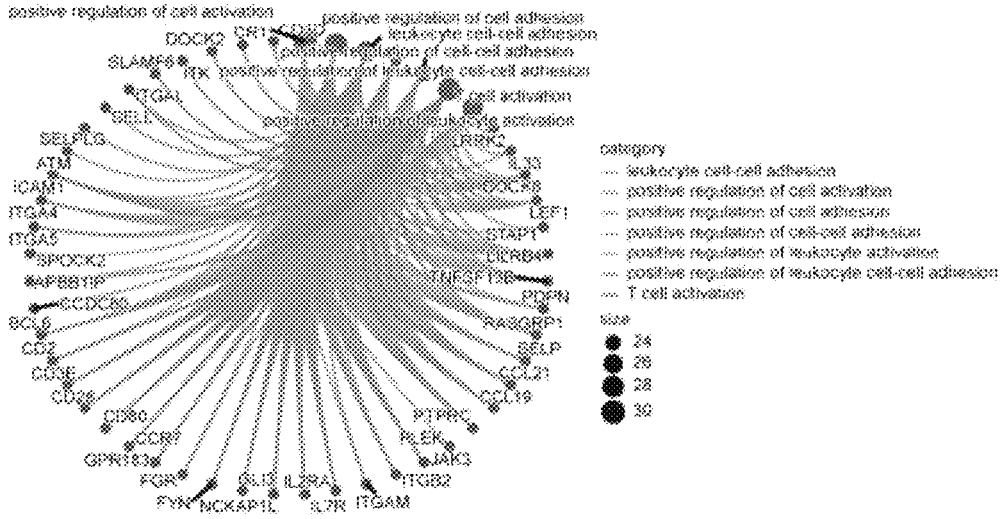
Figure 3C:
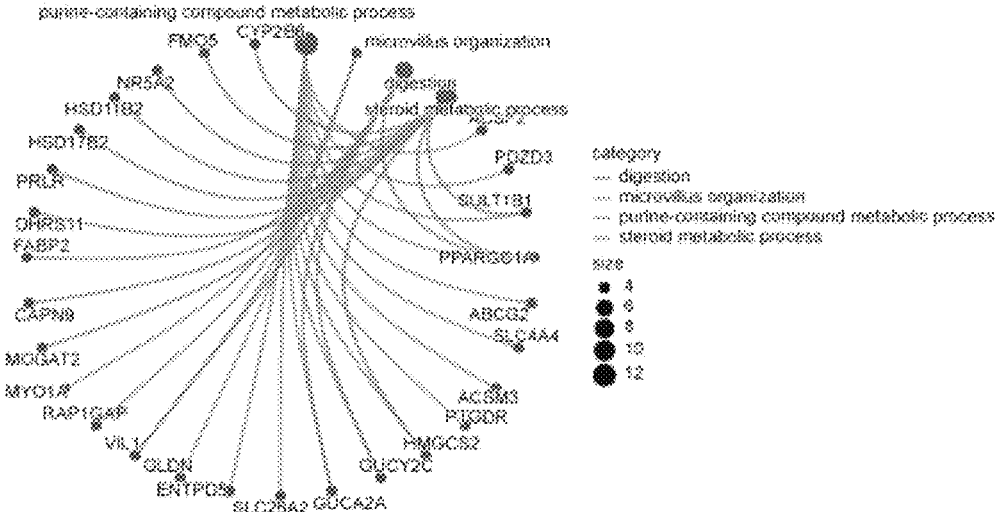
Figure 3D:
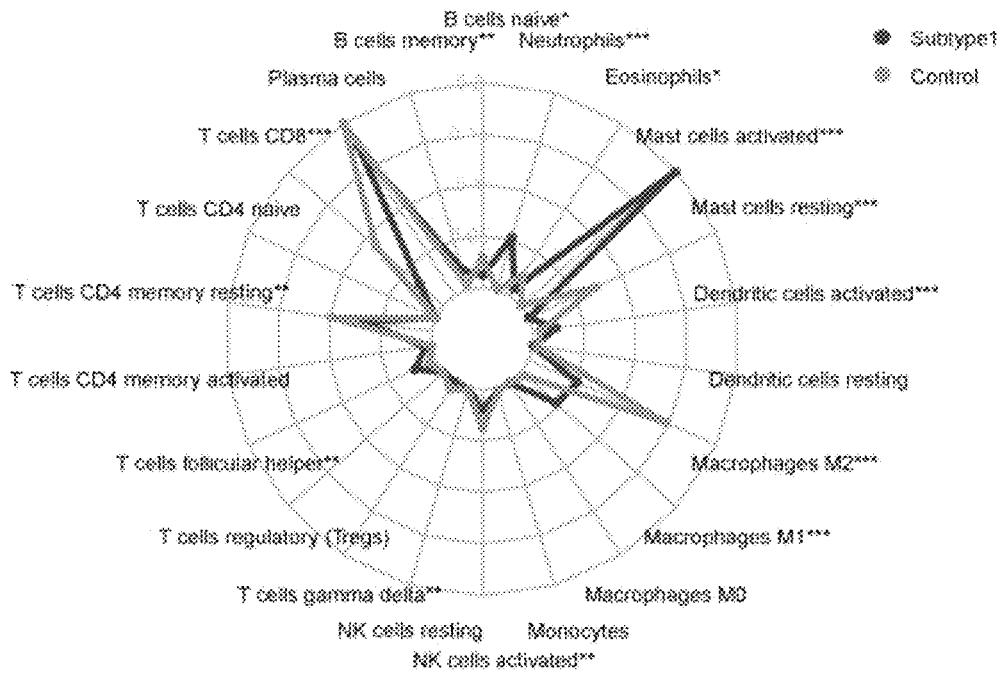
FIG. 3D, FIG. 3E, and FIG. 3F are schematic diagrams of results of CIBERSORT immune infiltration evaluation for three subtypes, respectively.
Figure 3E:
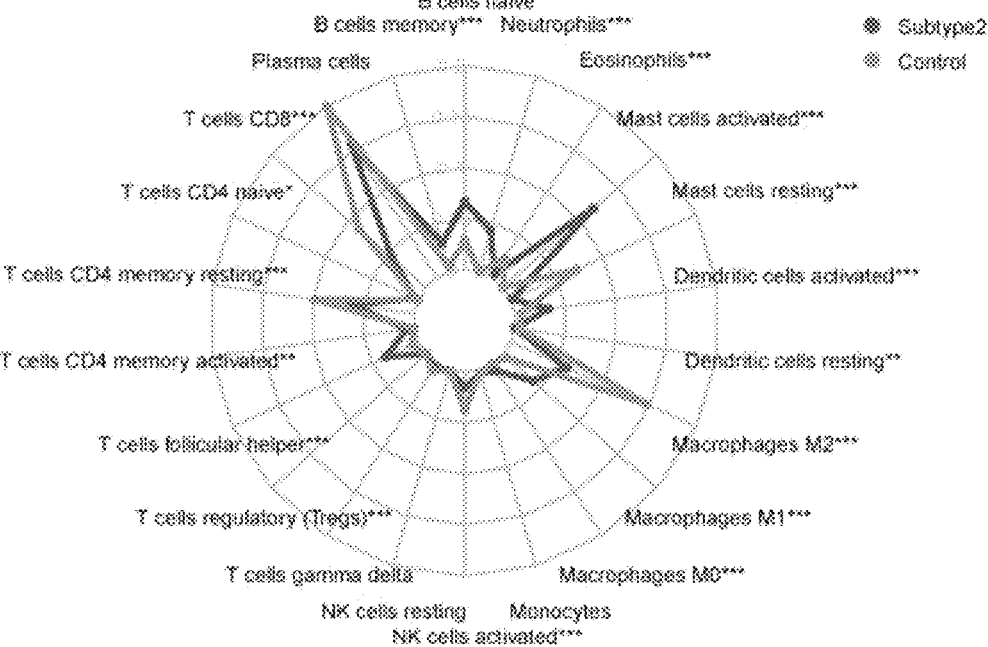
Figure 3F:
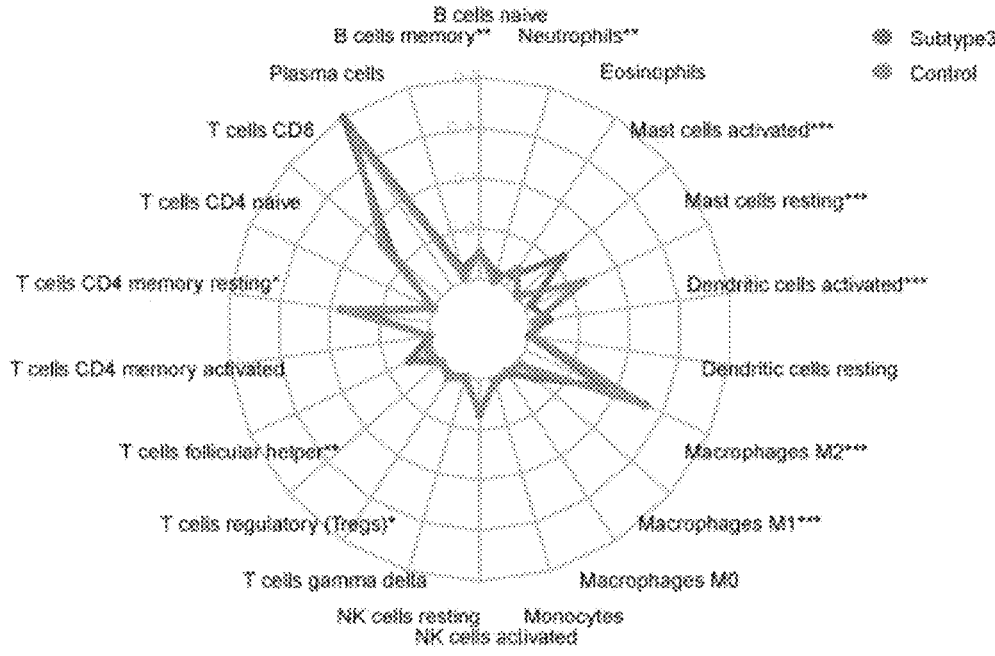
Figure 3G:
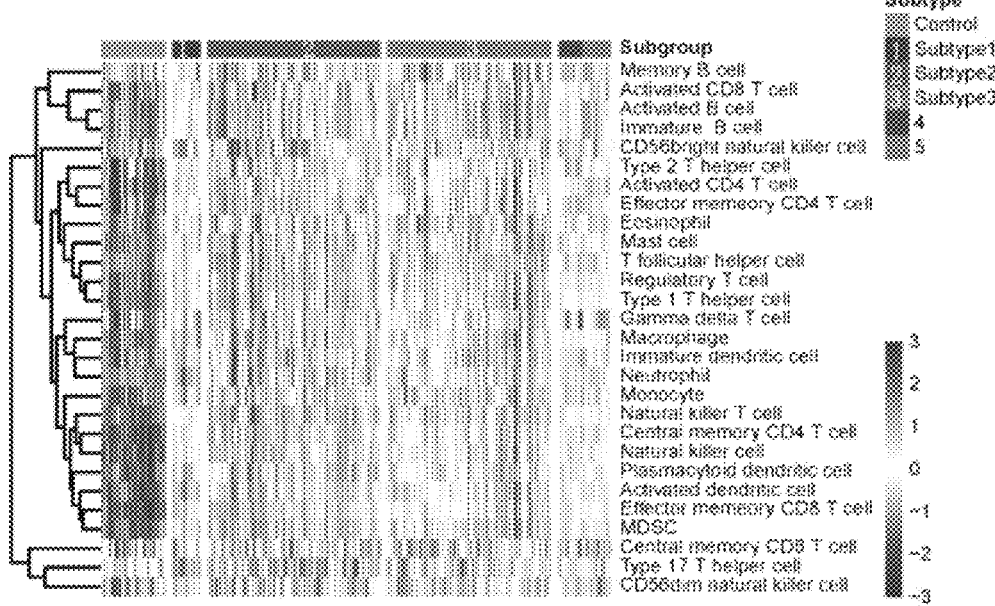
FIG. 3G is a schematic diagram of results of ssGSEA immune infiltration evaluation for subtypes.

The marker gene for each subtype is subjected to GO enrichment analysis. GO enrichment analysis results show that marker genes of cluster 1 are enriched in a neutrophil-activation pathway, genes of cluster 2 are enriched in a plurality of immune-activation pathways, and genes of cluster 3 are enriched in metabolism-associated pathways (FIGS. 3A-3C). The three datasets are subjected to batch effect removal and then merged into one dataset. According to CIBERSORT immune infiltration results, proportions of neutrophils and mast cells in cluster 1 are significantly larger than normal proportions of neutrophils and mast cells, and a proportion of immune cell infiltration in cluster 2 is significantly different from a normal proportion of immune cell infiltration, indicating the enhancement of activation of lymphocytes such as T cells and B cells. However, the immune infiltration in cluster 3 is similar to the immune infiltration in a normal mucosa (FIGS. 3D-3F). Immune infiltration evaluation results of ssGSEA show that immune cells exhibit a low immune cell abundance in cluster 3 (FIG. 3G). Accordingly, cluster 1 is named IIA, cluster 2 is named WIA, and cluster 3 is named IHL.

(3) Comparison of Subtypes in Terms of Severity and Treatment Response

Figure 4A:
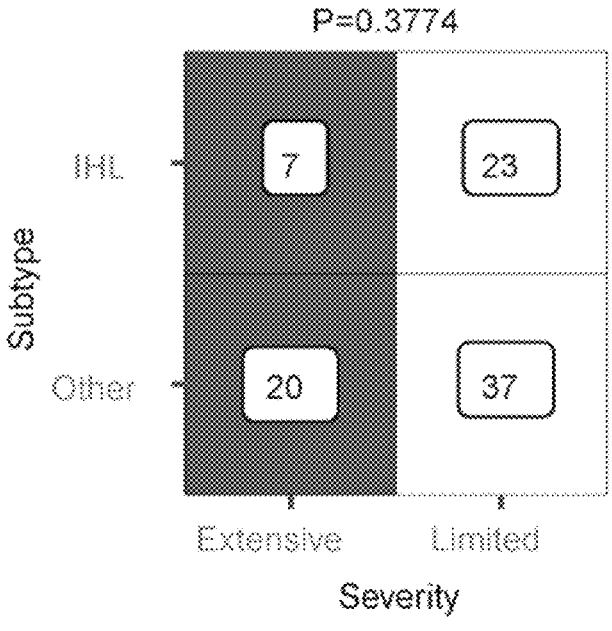
FIG. 4A is a schematic diagram of differences in disease severity between IHL-UC and other types of UC.
Figure 4B:
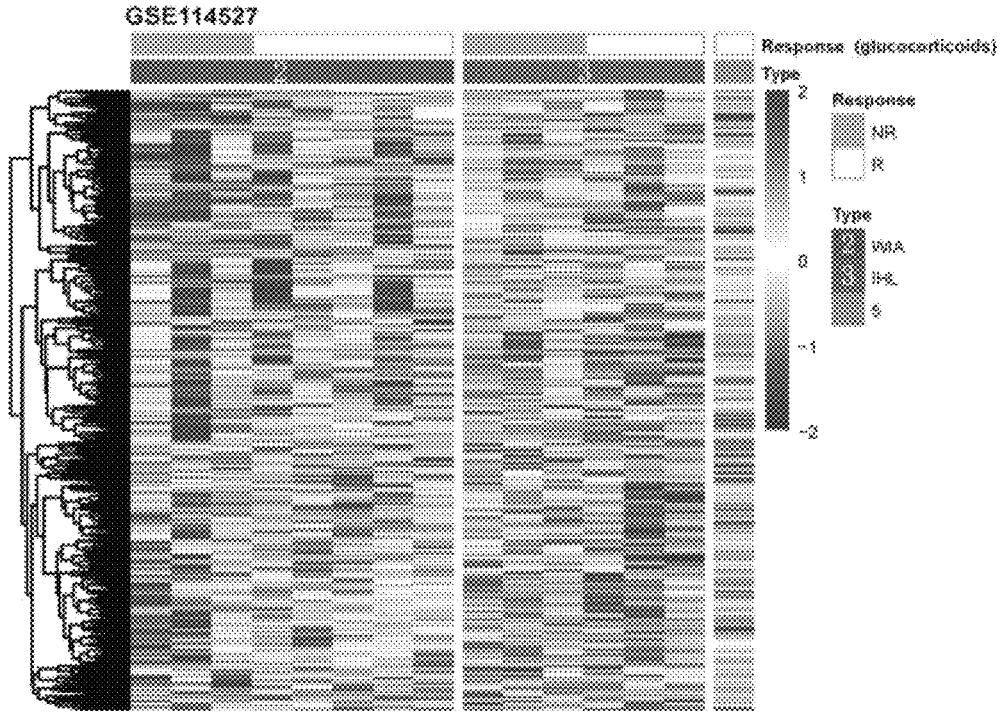
FIG. 4B is a schematic diagram of responses of subtypes to a glucocorticoid therapy.
Figure 4C:
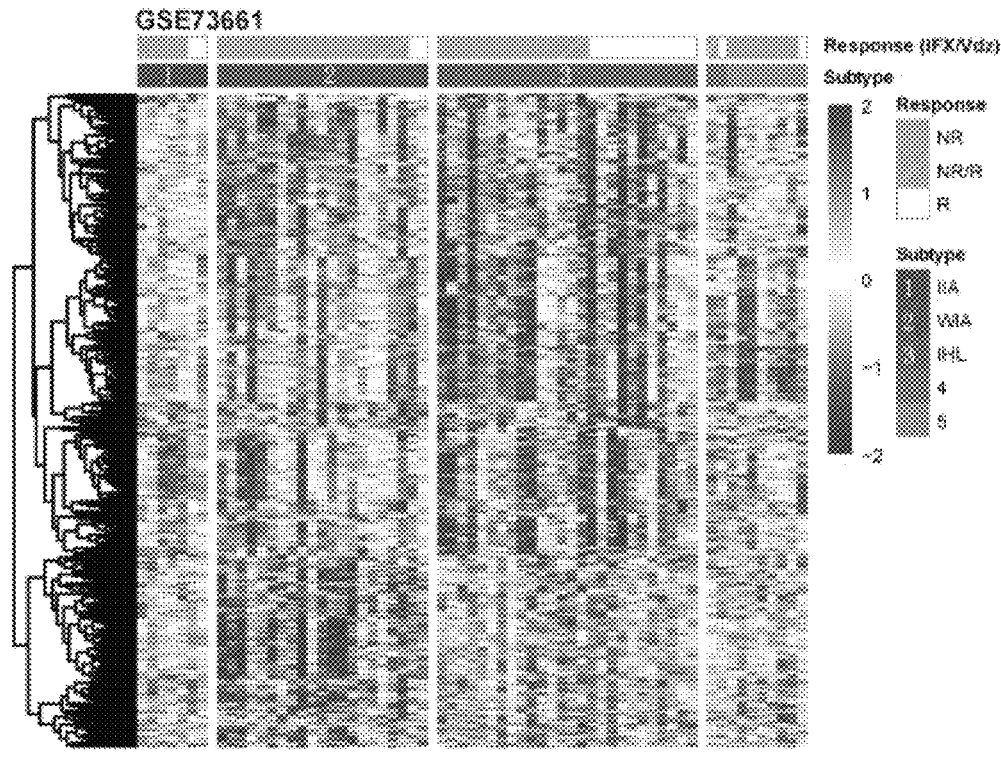
FIG. 4C is a schematic diagram of responses of different subtypes to infliximab (IFX) or vedolizumab (Vdz)
Figure 4D:
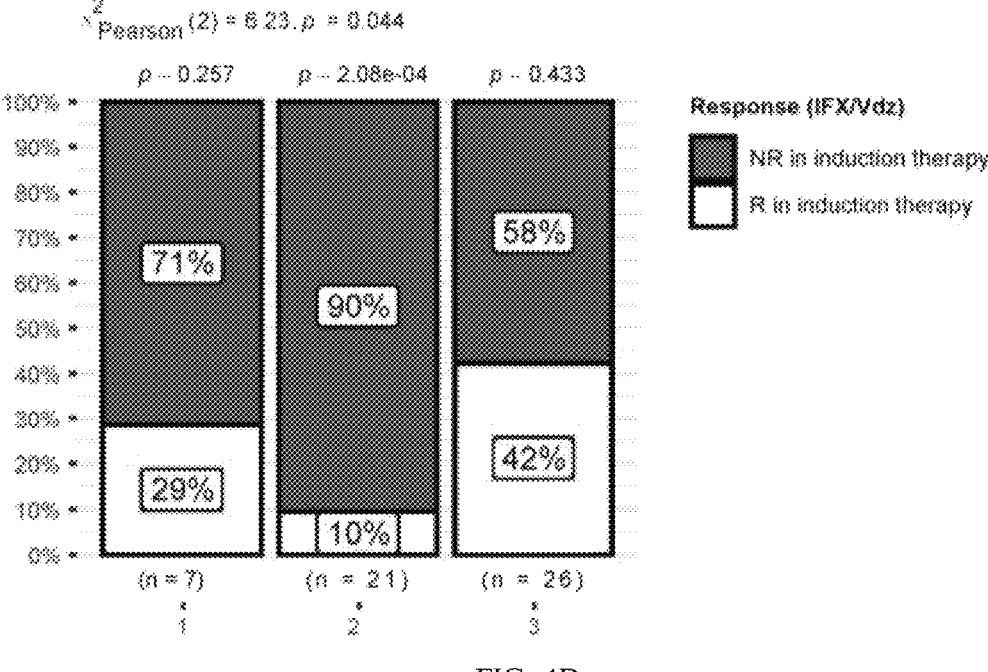
FIG. 4D is a schematic diagram of response rates and statistical tests of an IFX/Vdz therapy in GSE73661.
Figure 4E:
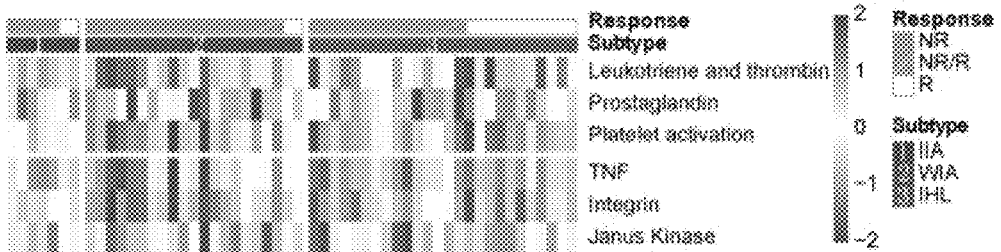
FIG. 4E is a schematic diagram of comparison of GSE73661 therapeutic targets among subtypes.
Figure 4F:
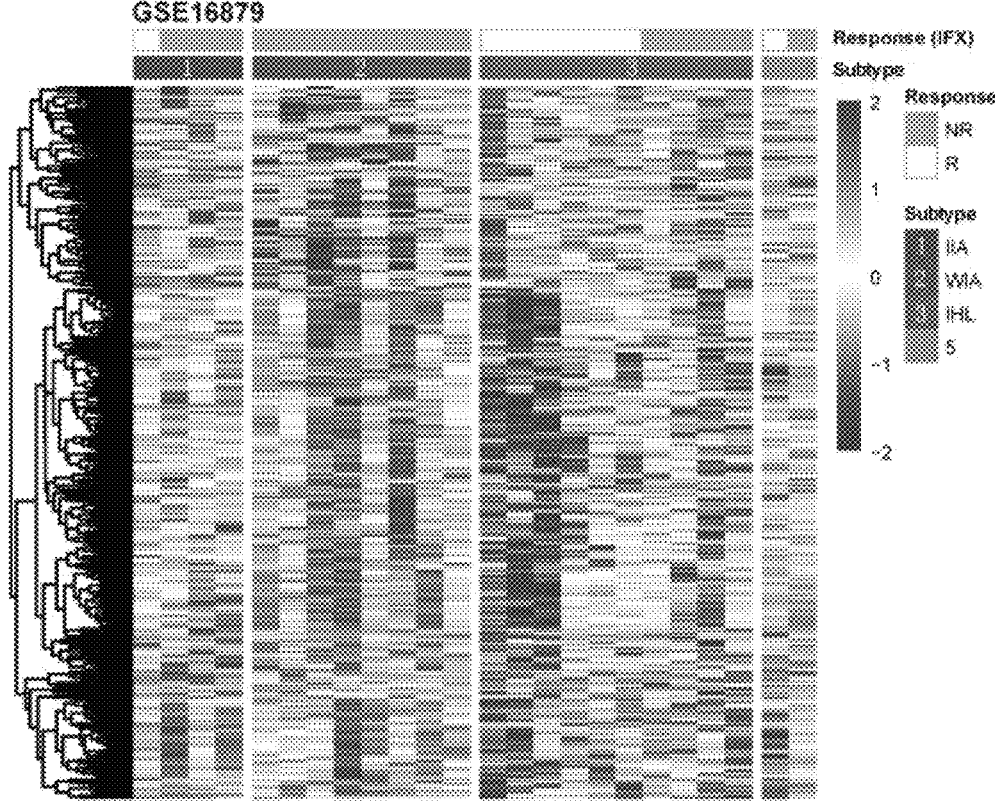
FIG. 4F is a schematic diagram of responses of different subtypes to an IFX therapy.

IHL-UC is compared with another subtype in terms of severity (extended or limited) according to clinical data, and results show that there is no statistical difference between the two groups (chi-square test: P=0.3774) (FIG. 4A), indicating that it is difficult to distinguish subtypes based on clinical manifestations alone. Responses of subtypes to a glucocorticoid therapy are compared in GSE114527, and results show that there is no difference among groups (FIG. 4B). Responses of subtypes to an IFX or Vdz therapy are compared in GSE73661, and results show that the WIA class has the worst efficacy (90% of cases have no response during the initial treatment) and the IHL class has the best treatment response rate (chi-square test: P=0.044) (FIG. 4C and FIG. 4D). Responses of subtypes to an IFX therapy are compared in GSE16879, and results show that the WIA class has the worst efficacy (100% of cases have no response) and the IHL class has the best treatment response rate (chi-square test: P=0.024) (FIG. 4F and FIG. 4G). Classical therapeutic targets (including leukotrienes, prostaglandins, thromboxanes, platelet activation pathways, or the like) and novel therapeutic targets (TNFs, integrins, Janus kinase pathways, or the like) are evaluated by ssGSEA, and results show that various therapeutic targets for the WIA class have a large abundance, and the compensation of different therapeutic pathways may be caused by non-response to biological agents (FIG. 4E and FIG. 4H).

(4) Development of Classifiers Based on Machine Learning

Figure 5A:
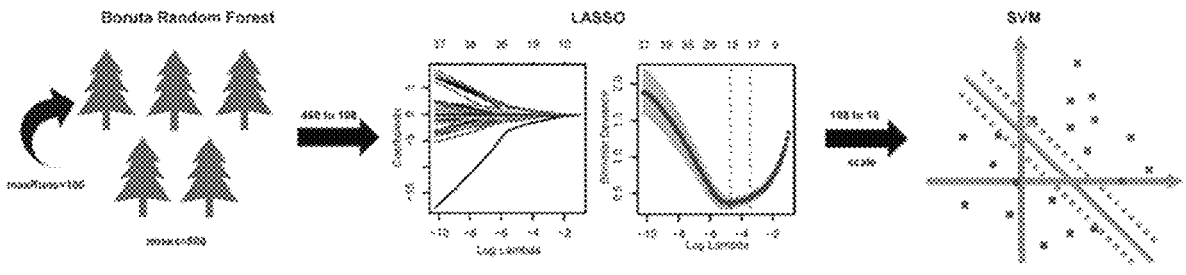
FIG. 5A is a schematic diagram of a work flow of machine learning.
Figure 5B:
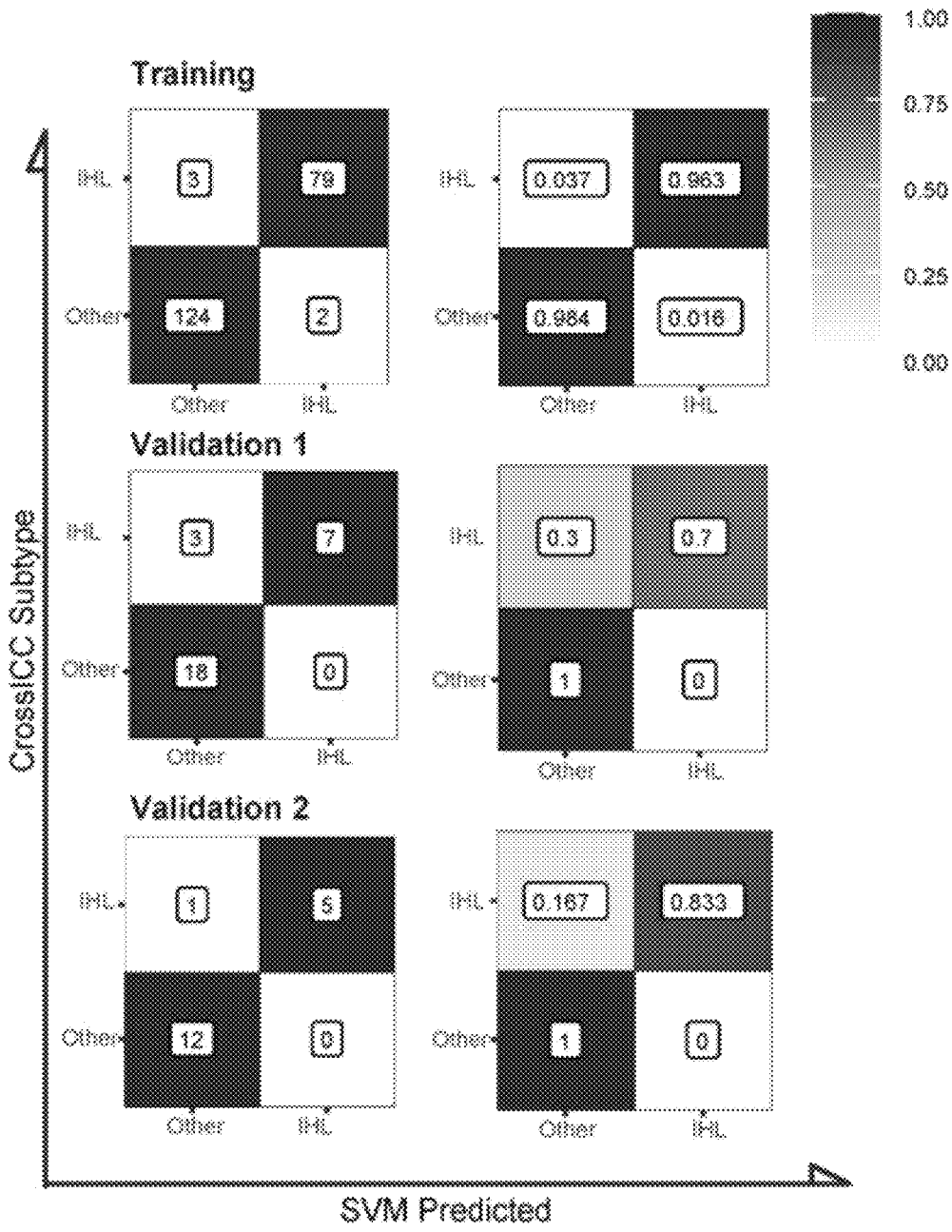
Figure 6A:
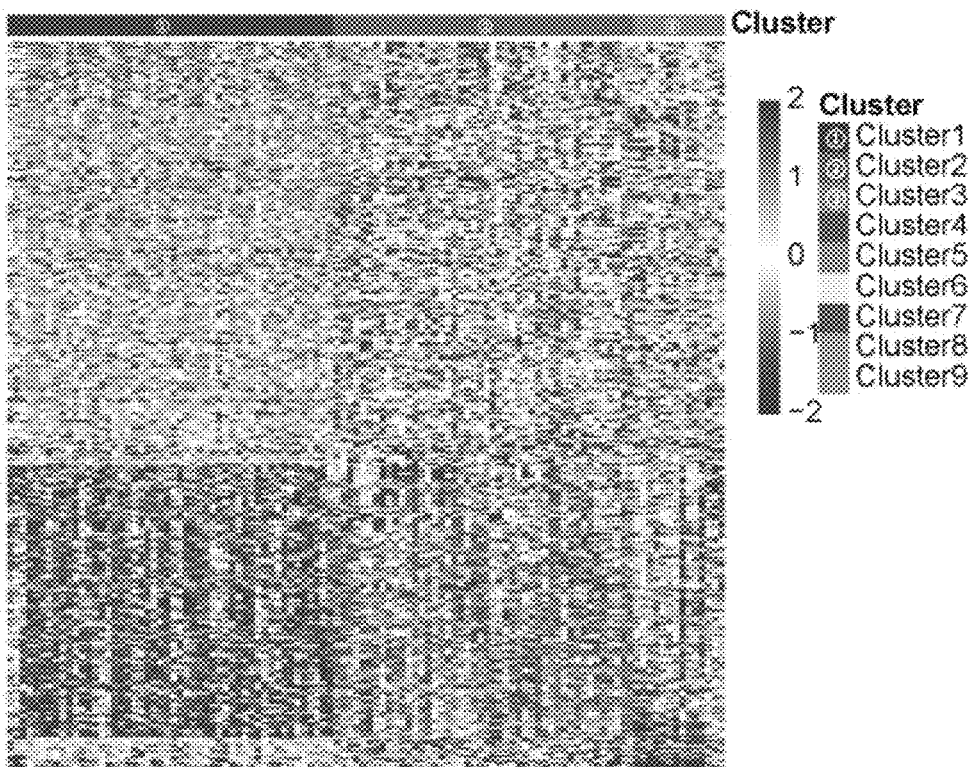
Figure 6B:
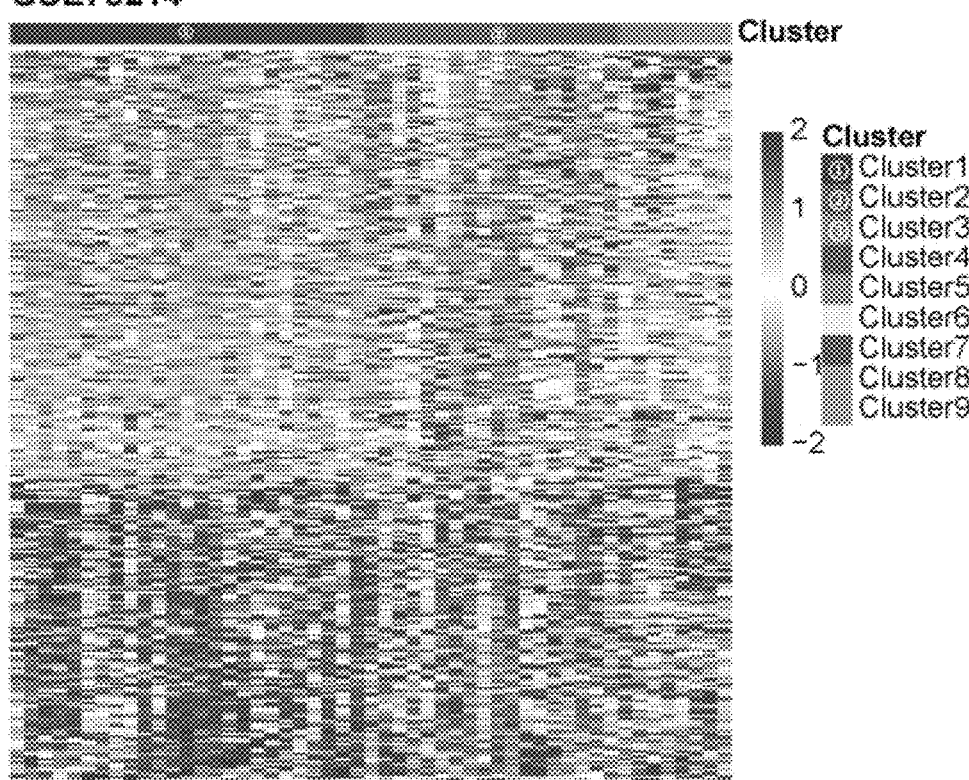
Figure 6C:
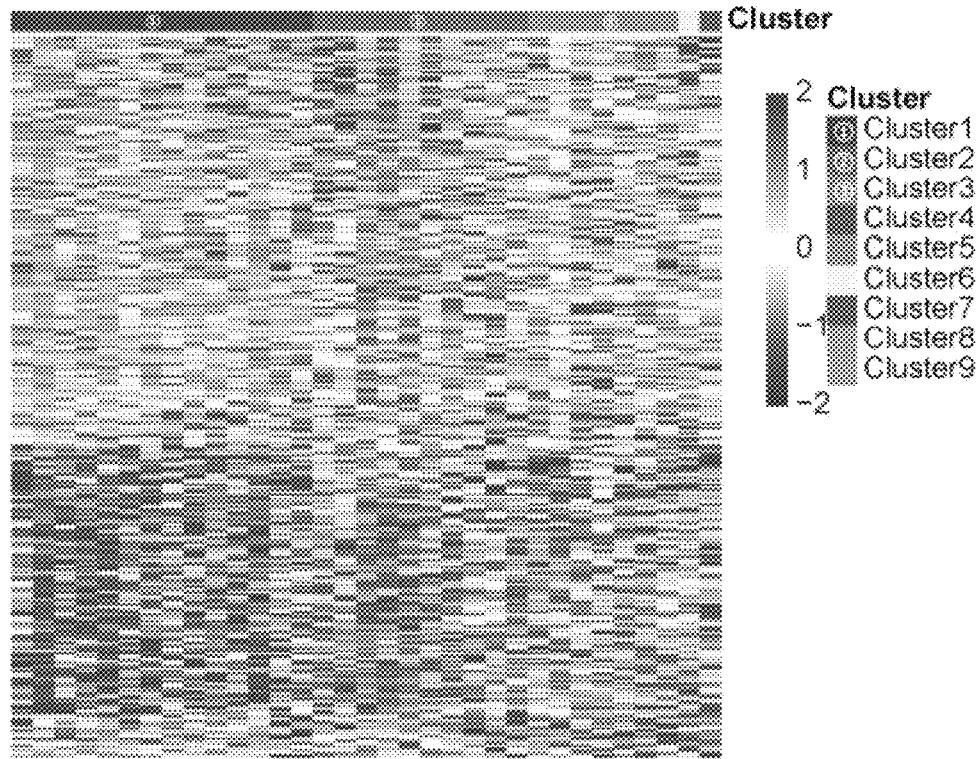
Figure 6D:
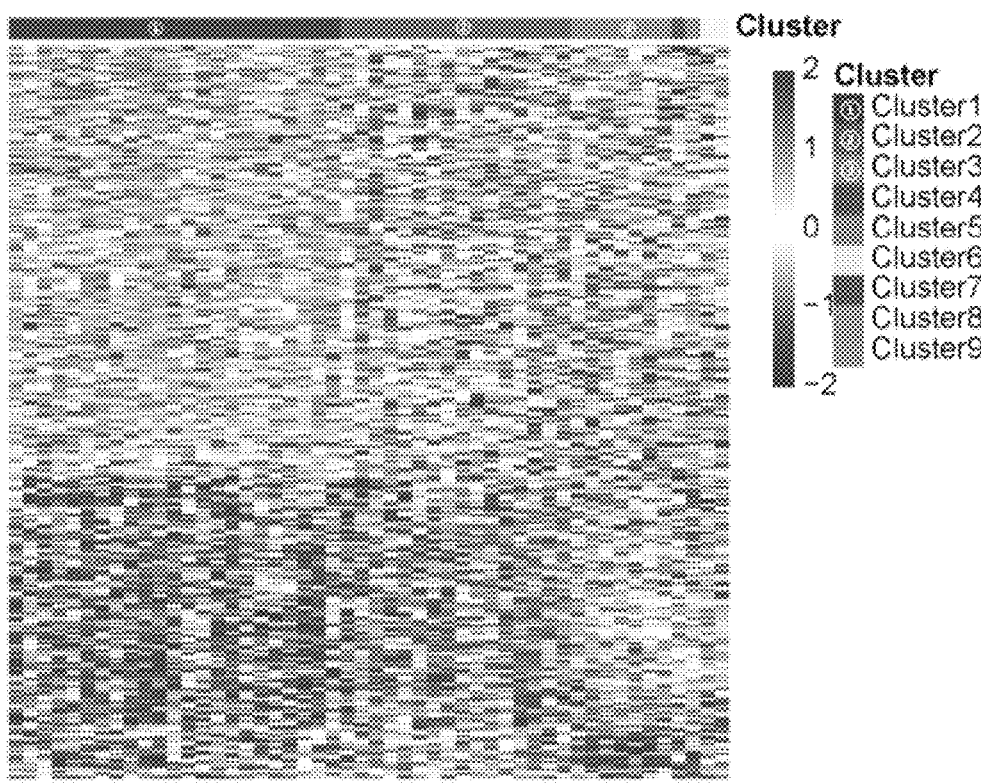

The above results show that, after IHL-UC is accurately identified in clinical practice, a biological agent can be used for IHL-UC in a targeted manner to ensure a high response rate, and the use of the biological agent for other subtypes should be avoided as much as possible to avoid a waste of medical resources to a maximum extent. Given that there are 460 marker genes in total, a few feature genes need to be selected to build a panel suitable for clinical practice. According to a learning flow (FIG. 5A), a total of 108 feature genes are retained by random forest, and 16 feature genes are left after Lasso regression of 10-fold cross-validation. The 10-fold cross-validation determines the optimal parameter combination for the support vector machine: a gamma value=0.1 and a cost value=1. After the support vector machine model is constructed, a prediction is conducted on a training set, and an accuracy is 97.5%. An accuracy is 89.3% on the external validation set of GSE83687, and an accuracy is 94.4% on the external validation set of GSE126124. This model has an excellent ability to distinguish IHL-UC from UC of other subtypes (FIG. 5B). In FIG. 5B, the left panel: a confusion matrix, and the right panel: a sensitivity, specificity, false positive rate, and false negative rate table.

Although the IHL class has similar clinical manifestations to other subtypes, a local immune cell infiltration profile of a lesion of the IHL class is close to a local immune cell infiltration profile of a normal mucosa. Clinical patients are subjected to molecular typing as above. Molecular typing results and prognosis analysis results show that, for a therapy with an immunobiologic agent such as TNF or anti-integrin, a response rate of patients with IHL-UC is nearly 50%, while a response rate of patients with WIA-UC is less than 10%, indicating that the identification of a UC subtype is conducive to the accurate selection of a clinical drug. Therefore, an IHL-UC classifier based on immune-related gene expression profiles is constructed through a machine learning flow of random forest, regularization, and a support vector machine, and an accuracy of 97.5% and an accuracy of 89.3% to 94.4% are allowed in a training set and a validation set, respectively, which allows the accurate and rapid identification of IHL-UC and facilitates the accurate treatment of UC.

It should be noted that, in the analysis and evaluation step of this example, according to actual analysis results, the obtained subtypes are divided into the following three subtype classes: an IIA class, a WIA class, and an IHL class. During the comparison of treatment responses, it is found that the IHL class has a high response rate to a biological agent. Therefore, when a support vector machine is constructed subsequently, only an IHL class with a high response rate needs to be identified, which facilitates the subsequent targeted use of a biological agent. When other treatment modes are adopted, subtypes of other classes may have a high response rate, that is, as long as a subtype class with a high response rate under a specified treatment mode is identified, the targeted treatment can be allowed according to an identification result during the subsequent treatment process.

In view of this, those skilled in the art have a reason to consider that, in the analysis and evaluation step, it is enough to simply divide the subtypes into an IHL class and other subtype classes. It is also possible to divide the subtypes into a plurality of classes and then identify one or more classes with a higher treatment response rate than a target value by a support vector machine. Thus, the subtypes can also be divided into an immune activation class (the IIA class and the WIA class described above are combined) and an immune homeostasis class, or into an IHL class and other classes of an unlimited number. The present disclosure has no restriction on specific subtype classes to be identified, and those skilled in the art can determine a corresponding subtype class according to a treatment mode and a treatment response rate.

Example 2: CD

A method of molecular typing and subtyping classifier for CD is provided, including:

A data acquisition step: A CD microarray dataset is acquired and divided into a training set, a validation set, and a comparison set. In the present disclosure, the CD microarray dataset is acquired from a GEO database, where GSE112366 (n=110), GSE75214 (n=51), GSE179285 (n=33), and GSE100833 (n=50) are adopted as a training set, GSE16879 (n=18) is adopted as a typing validation set, and GSE112366 (n=66) is adopted to compare treatment response rates. Only tissues from terminal ilea are included, and only mucosal tissues involved by active CD are included. In addition, normal samples are retained as a control group. A total of 244 mucosal tissues are included in the training set. Any data is transformed by log 2.

A molecular typing step: Molecular typing is conducted via a clustering algorithm in the training set to obtain a plurality of subtypes stably appearing in the training set and a marker gene for each subtype, and a stability of typing training results is verified through the validation set. In the present disclosure, a CrossICC algorithm is used to conduct training with the training sets of GSE112366, GSE75214, GSE179285, and GSE100833 to obtain subtypes and a marker gene for each subtype. Typing results are predicted on the validation set of GSE16879, and whether the typing results are stable is observed. If a typing result is not stable, dataset selection and quality control are required once again for the training set.

An analysis and evaluation step: Marker genes for the plurality of subtypes are subjected to enrichment analysis, the plurality of subtypes are subjected to immune cell infiltration evaluation, and the plurality of subtypes are divided into an IHL class, an IIA class, and an intermediate class according to results of the enrichment analysis and the immune cell infiltration evaluation. In the present disclosure, the marker gene for each subtype is subjected to enrichment analysis with a clusterProfiler package, and each subtype is subjected to immune cell infiltration evaluation with CIBERSORT and ssGSEA.

A comparison step: Treatment response rates of different subtypes are compared through the comparison set. Response data of a biological agent therapy of ustekinumab (an IL-12/IL-23 inhibitor) in GSE112366 is downloaded, and only mucosal expression profile data before drug administration is used for subtype identification. If different subtypes have different drug treatment effects, it can indicate a clinical value of the molecular typing of the present disclosure and the necessity for constructing a classifier for clinical practice.

A classifier construction step: A support vector machine model is constructed with feature genes selected from the marker genes and an optimal parameter combination for a support vector machine. According to results of CrossICC, samples are divided into the following two classes: an IHL class and other subtypes. Based on marker genes for all subtypes, a maximum number of runs is set to 1,000 and a number of trees is set to 500 by a random forest method in a Boruta package, and feature genes left after screening are input into Lasso regression of 10-fold cross-validation to leave genes with non-zero parameters as the final feature genes. The support vector machine method is used for subtype determination. Before each execution of the support vector machine, feature genes in each sample are normalized (scale) to avoid the influence of a feature gene with a too-large standard deviation on a support vector. After the support vector machine model is generated, a prediction and an evaluation are conducted in a training set and two external validation sets. The performance of classifying is evaluated by a confusion matrix, where:

an accuracy=samples correctly classified/total samples;

a sensitivity=a number of positive samples correctly classified/a total number of positive samples;

a specificity=a number of negative samples correctly classified/a total number of negative samples;

a false positive rate=negative samples determined to be positive/a total number of negative samples; and a false negative rate=positive samples determined to be negative/a total number of positive samples.

A statistical analysis step: A Wilcoxon test is used to compare means of two groups of continuous variables. A Kruskal-Wallis test is used to compare means of a plurality of groups of continuous variables. A chi-square test or a Fisher's exact test is adopted for classification variables. Any statistical analysis is conducted in R (version 4.0.3).

A classifying step: CD data to be classified is input into the support vector machine model to determine whether the CD data to be classified is an IHL class.

Experimental Results (1) Three Stable Molecular Subtypes of CD are Identified by CrossICC.

A series of subtypes are identified by the CrossICC algorithm in the three datasets of GSE112366, GSE75214, GSE179285, and GSE100833, where cluster 1 and cluster 2 stably appear in each dataset (FIGS. 6A-6D). A marker gene for each subtype is obtained. To confirm a stability of typing, the two external validation sets are used for subtype validation, and results show that subtypes of cluster 1 and cluster 2 are also available in these two datasets according to marker genes, and cluster 3 is also an important subtype (FIG. 2E).

(2) Enrichment Analysis and Immune Infiltration of Subtypes

Figure 7A:
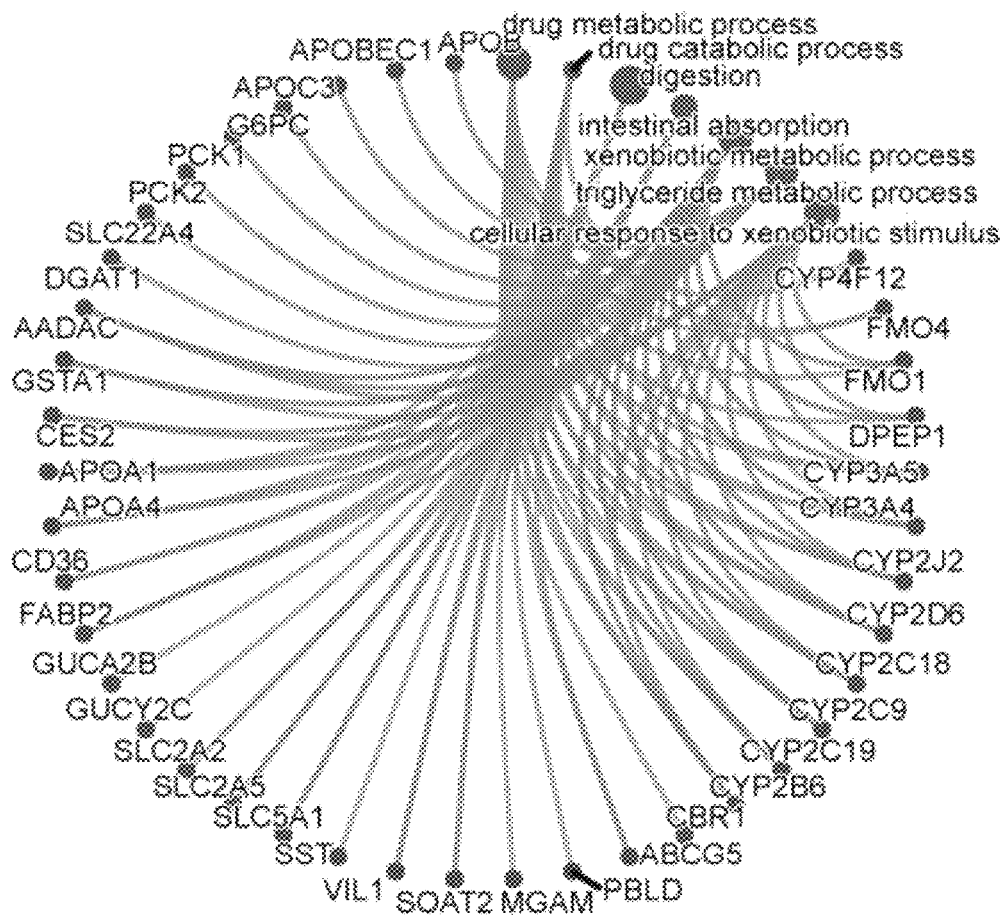
FIG. 7A and FIG. 7B are schematic diagrams of results of GO enrichment analysis for the first two major subtypes, respectively.
Figure 7B:
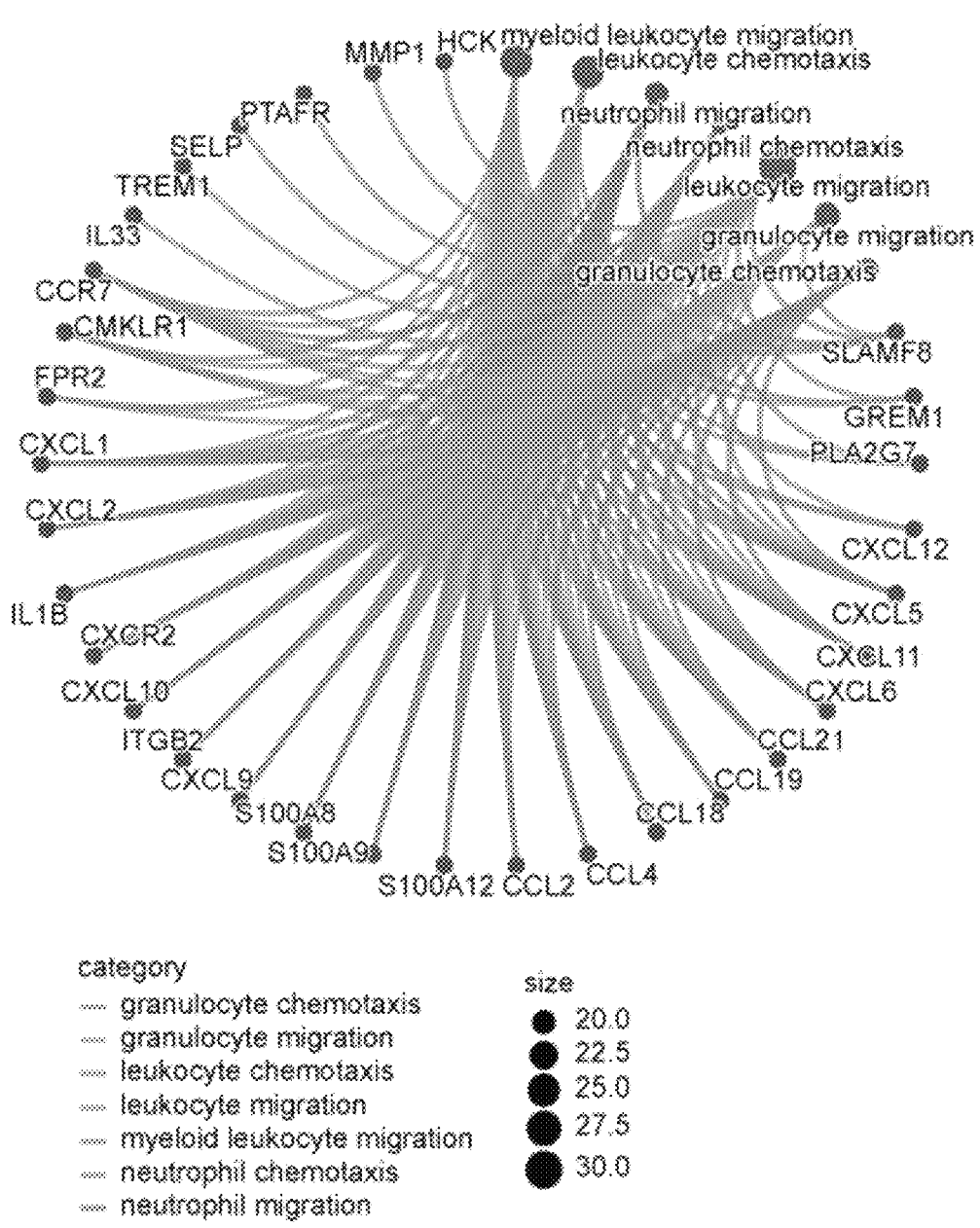
Figure 7C:
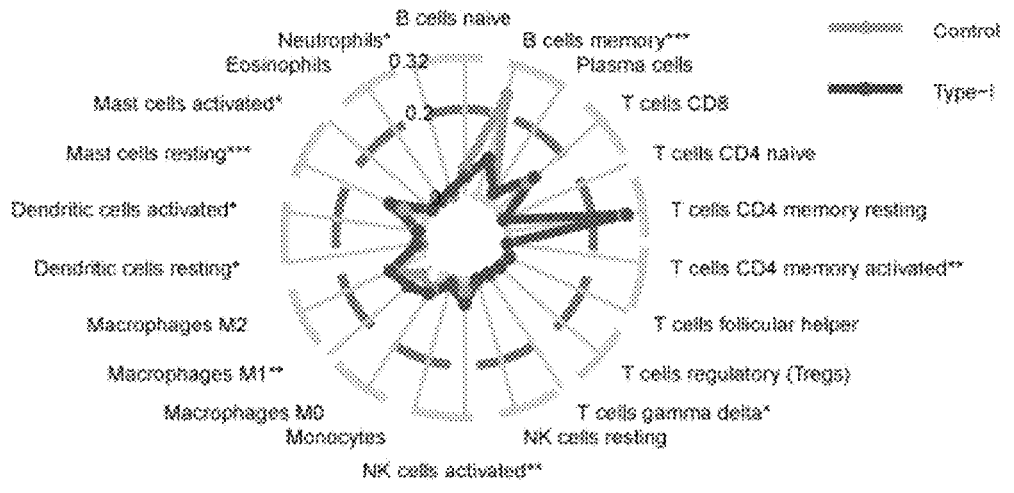
FIG. 7C, FIG. 7D, and FIG. 7E are schematic diagrams of results of CIBERSORT immune infiltration evaluation for three subtypes, respectively.
Figure 7D:
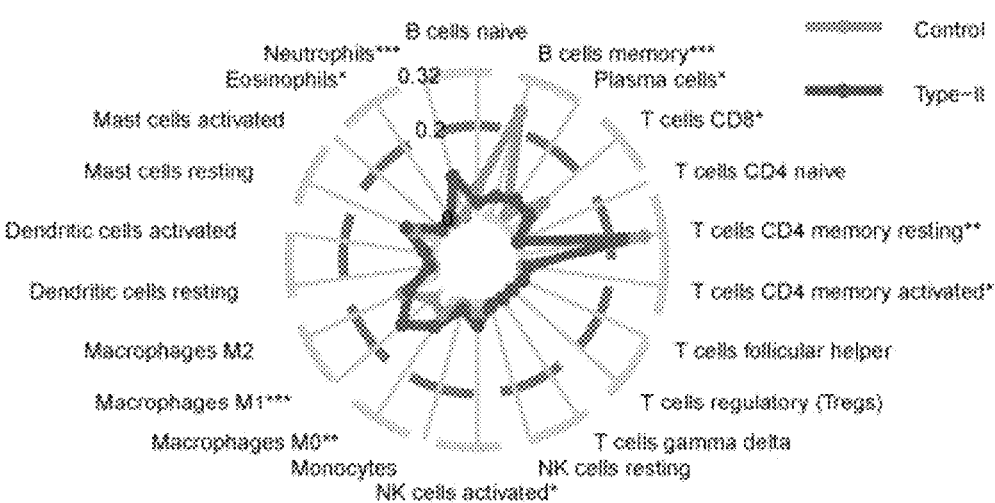
Figure 7E:
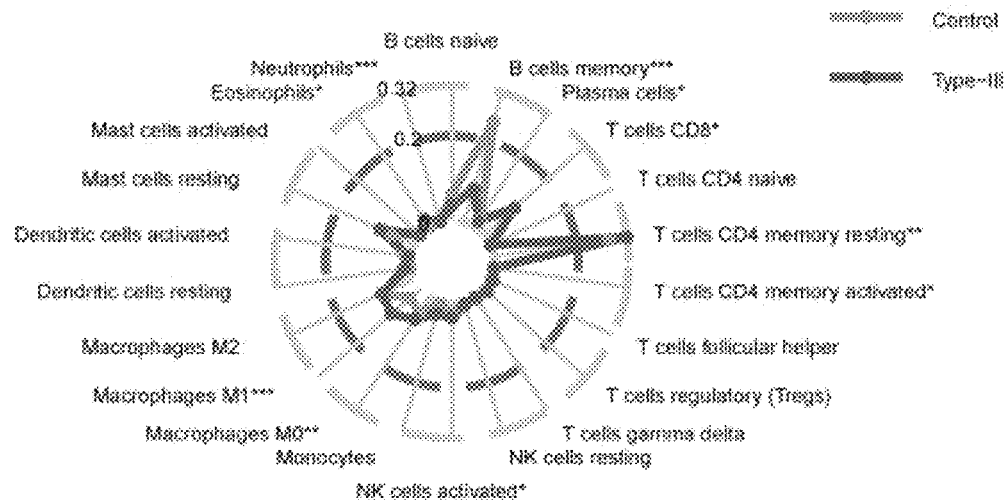
Figure 7F:
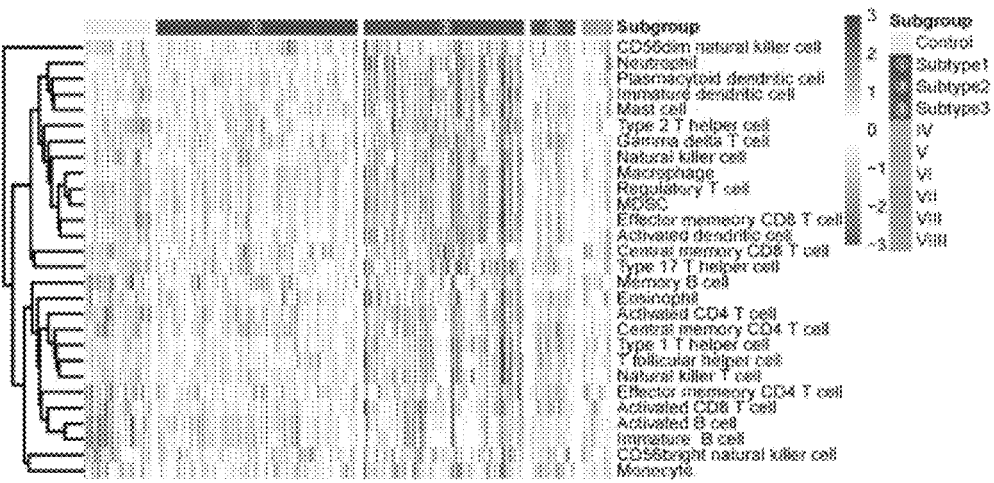
FIG. 7F is a schematic diagram of results of ssGSEA immune infiltration evaluation for subtypes.

The marker gene for each subtype is subjected to GO enrichment analysis. GO enrichment analysis results show that marker genes of cluster 1 are enriched in metabolism-associated pathways, and genes of cluster 2 are enriched in myeloid and neutrophil activation pathways (FIGS. 7A-7B). The four datasets are subjected to batch effect removal and then merged into one dataset. CIBERSORT immune infiltration results show that there is no significant activation of immune cells in cluster 1, there is significant activation of neutrophils and MI macrophages in cluster 2, and the immune infiltration of cluster 3 is between the immune infiltration of cluster 1 and the immune infiltration of cluster 2 (FIGS. 7C-7E). Immune infiltration evaluation results of ssGSEA show that immune cells exhibit a low immune cell abundance in cluster 1 (FIG. 7F). Accordingly, cluster 1 is named IHL, cluster 2 is named IIA, and cluster 3 is named intermediate.

(3) Comparison of Subtypes in Terms of Severity and Treatment Response

Figure 8A:
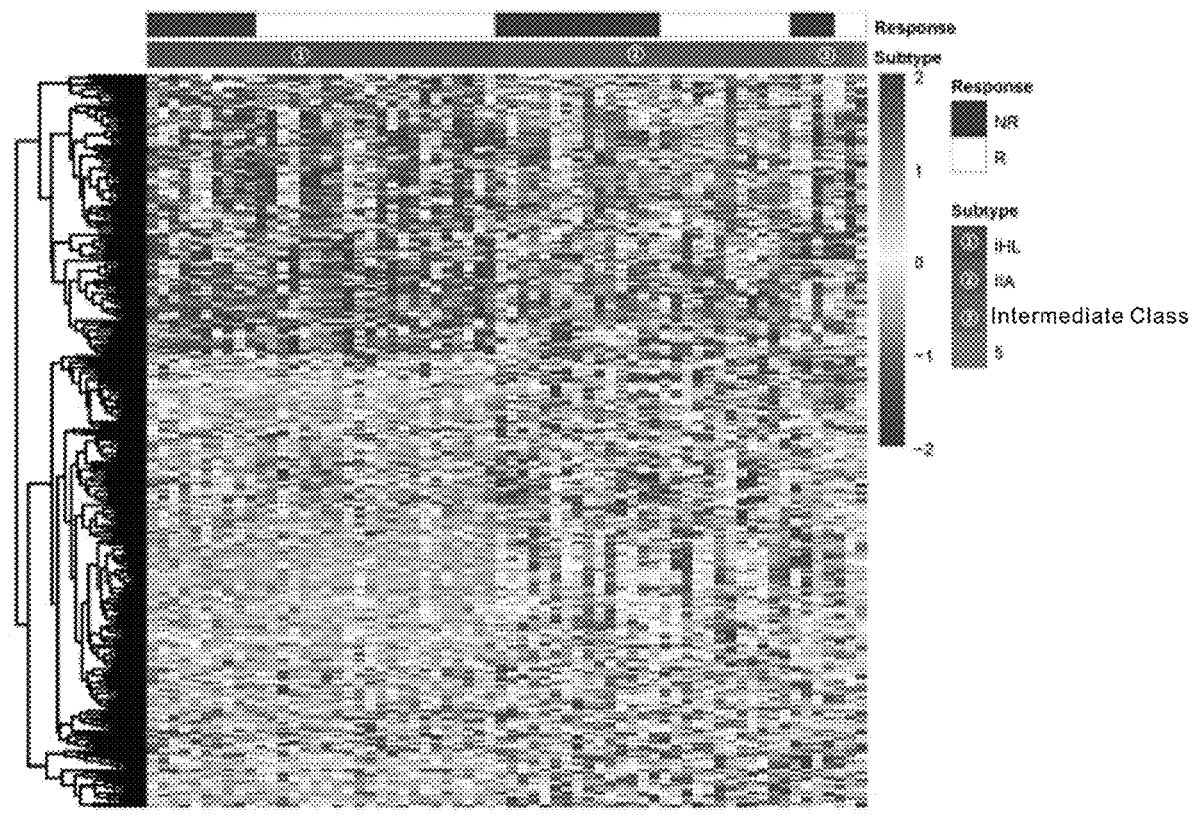
FIG. 8A is a schematic diagram of responses of different subtypes of CD to a ustekinumab therapy.
Figure 8B:
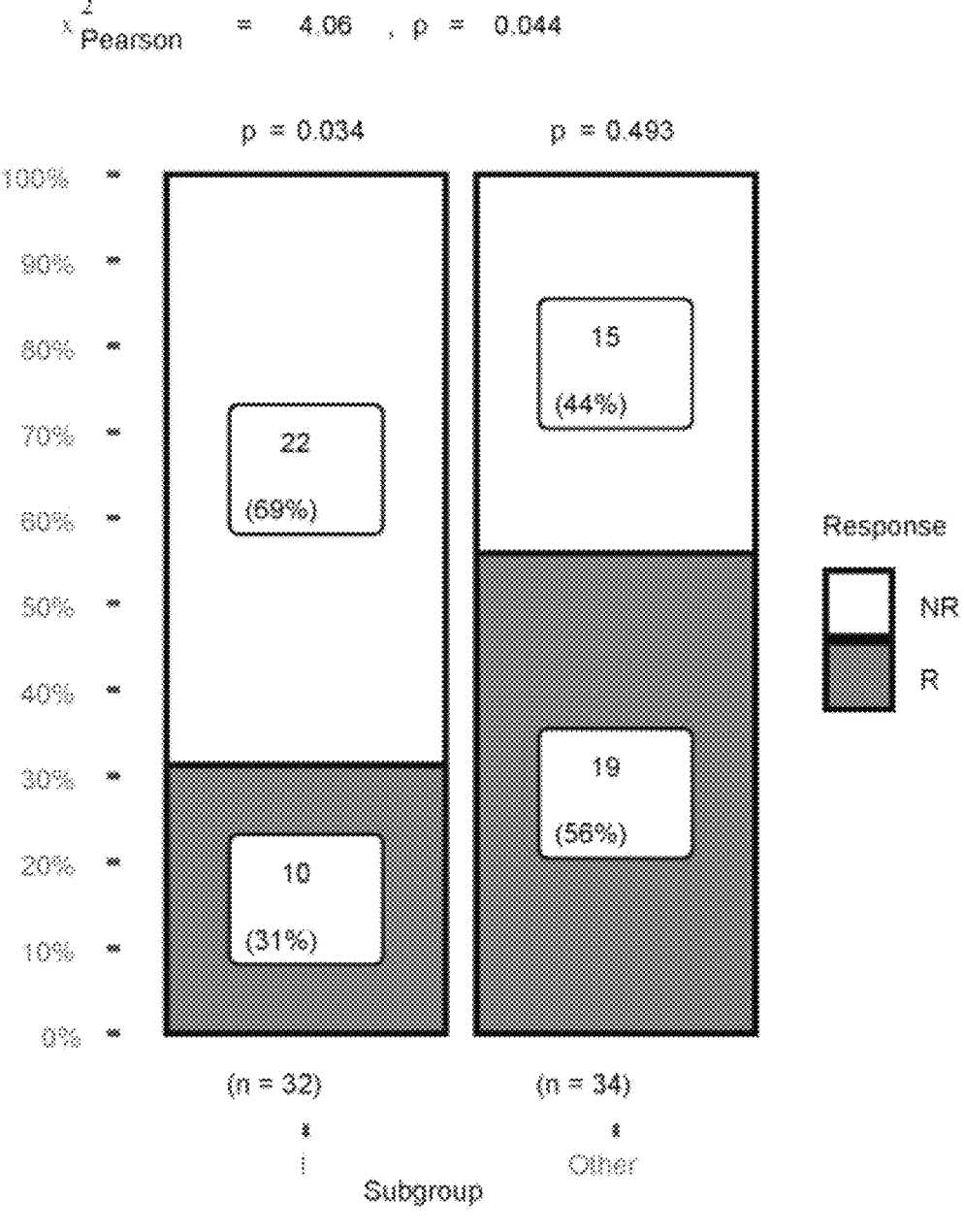
FIG. 8B is a schematic diagram of response rates and statistical tests of a ustekinumab therapy in GSE112366.

Responses of subtypes to an ustekinumab therapy are compared in GSE16879, and results show that the IHL class has the optimal treatment response rate (chi-square test: P=0.044) (FIG. 8A and FIG. 8B).

(4) Development of Classifiers Based on Machine Learning

Figure 9:
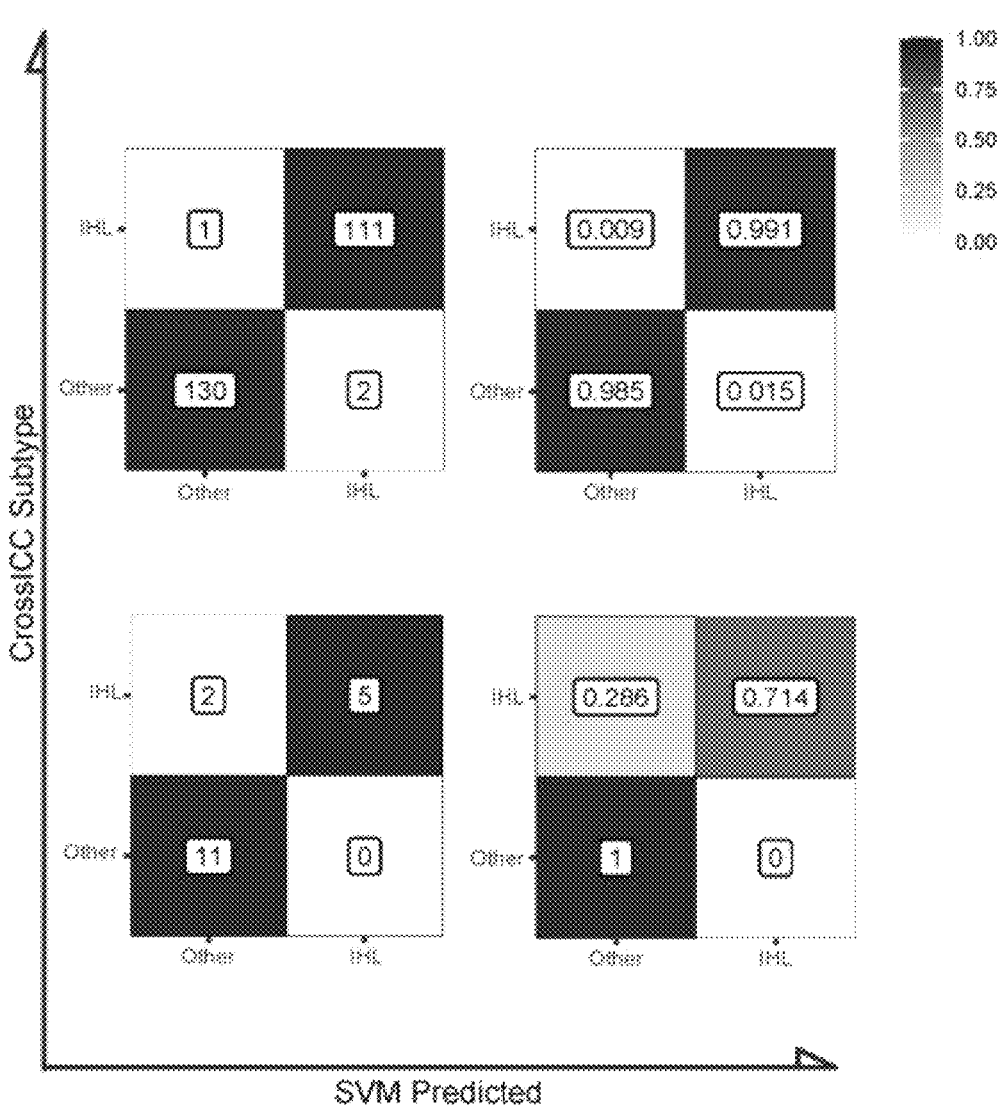

The above results show that, after IHL-CD is accurately identified in clinical practice, a biological agent can be used for IHL-CD in a targeted manner to ensure a high response rate, and the use of the biological agent for other subtypes should be avoided as much as possible to avoid a waste of medical resources to a maximum extent. Given that there are 273 marker genes in total, a few feature genes need to be screened out to build a panel suitable for clinical practice. According to a learning flow, a total of 130 feature genes are retained by random forest, and 24 feature genes are left after Lasso regression of 10-fold cross-validation. The 10-fold cross-validation determines the optimal parameter combination for the support vector machine: a gamma value=0.01 and a cost value=1. After the support vector machine model is constructed, a prediction is conducted on a training set, and an accuracy is 98.8%. On the external validation set of GSE16879, an accuracy is 88.9%. This model has an excellent ability to distinguish IHL-CD from CD of other subtypes (FIG. 9). In FIG. 9, the left panel: a confusion matrix, and the right panel: a sensitivity, specificity, false positive rate, and false negative rate table.

Although IHL-CD has similar clinical manifestations to other subtypes, a local immune cell infiltration profile of a lesion of the IHL-CD is close to a local immune cell infiltration profile of a normal mucosa. Clinical patients are subjected to molecular typing as above. Molecular typing results and prognosis analysis results show that, during an immunobiologic agent therapy, a response rate of patients with IHL-CD is nearly 70%, while a response rate of patients with CD of other subtypes is low, indicating that the identification of a CD subtype is conducive to the accurate selection of a clinical drug. Therefore, an IHL-CD classifier based on immune-related gene expression profiles is constructed through a machine learning flow of random forest, regularization, and a support vector machine, and an accuracy of 88.9% to 98.8% is allowed in a training set and a validation set, which allows the accurate and rapid identification of IHL-CD and facilitates the accurate treatment of CD.

It should be noted that, in the analysis and evaluation step of this example, according to actual analysis results, the obtained subtypes are divided into the following three subtype classes: an IIA class, an intermediate class, and an IHL class. During the comparison of treatment responses, it is found that the IHL class has a high response rate to a biological agent. Therefore, when a support vector machine is constructed subsequently, only an IHL class with a high response rate needs to be identified, which facilitates the subsequent targeted use of a biological agent. When other treatment modes are adopted, subtypes of other classes may have a high response rate, that is, as long as a subtype class with a high response rate under a specified treatment mode is identified, the targeted treatment can be allowed according to an identification result during the subsequent treatment process.

In view of this, those skilled in the art have a reason to consider that, in the analysis and evaluation step, it is enough to simply divide the subtypes into an IHL class and other subtype classes. It is also possible to divide the subtypes into a plurality of classes and then identify one or more classes with a higher treatment response rate than a target value by a support vector machine. Thus, the subtypes can also be divided into an IHL class and other classes of an unlimited number. The present disclosure has no restriction on specific subtype classes to be identified, and those skilled in the art can determine a corresponding subtype class according to a treatment mode and a treatment response rate.

The above two embodiments are illustrated with UC and CD as examples, respectively, but those skilled in the art should understand that the present disclosure can be applied to the molecular typing of immune-related diseases in other fields, which is not limited in the present disclosure.

A system of molecular typing and subtyping classifier for immune-related diseases is provided in the present disclosure, including:

a data acquisition module configured to: acquire an immune-related disease microarray dataset and divide the immune-related disease microarray dataset into a training set, a validation set, and a comparison set;

a molecular typing module configured to: conduct molecular typing via a clustering algorithm in the training set to obtain a plurality of subtypes stably appearing in the training set and a marker gene for each subtype, and verify a stability of molecular typing results through the validation set;

an analysis and evaluation module configured to: conduct enrichment analysis on marker genes for the plurality of subtypes, conduct immune cell infiltration evaluation on the plurality of subtypes, and divide the plurality of subtypes into a plurality of subtype classes according to results of the enrichment analysis and the immune cell infiltration evaluation;

a comparison module configured to: compare treatment response rates of different subtype classes through the comparison set to determine a subtype class to be identified;

a classifier construction module configured to: construct a support vector machine model with feature genes selected from the marker genes and an optimal parameter combination for a support vector machine; and a classifying module configured to: input immune-related disease data to be classified into the support vector machine model to determine whether the immune-related disease data to be classified is the subtype class to be identified.

Those skilled in the art are aware that, in addition to being implemented with a pure computer-readable program code, the system and each apparatus, module, and unit thereof provided in the present disclosure can allow a same program in a form of a logic gate, a switch, an application-specific integrated circuit, a programmable logic controller, or an embedded microcontroller by performing logic programming on the method steps. Therefore, the system and each apparatus, module, and unit thereof provided in the present disclosure can be regarded as a kind of hardware component. The apparatus, module, and unit included therein for realizing each function can also be regarded as a structure in the hardware component; and the apparatus, module, and unit for realizing each function can also be regarded as a software module for implementing the method or a structure in the hardware component.

Although specific implementations of the present disclosure are described above, those skilled in the art should understand that these are merely examples, and various changes or modifications can be made to these implementations without departing from the principle and essence of the present disclosure. Therefore, the claimed scope of the present disclosure shall be defined by the appended claims.

What is claimed is:

1. A method of molecular typing and subtyping classifications for immune-related diseases, comprising:

a data acquisition step: acquiring an immune-related disease microarray dataset and dividing the immune-related disease microarray dataset into a training set, a validation set, and a comparison set;

a molecular typing step: conducting the molecular typing via a clustering algorithm in the training set to obtain a plurality of subtypes stably appearing in the training set and a marker gene for each of the plurality of subtypes, and verifying a stability of molecular typing results through the validation set;

an analysis and evaluation step: conducting an enrichment analysis on the marker gene for each of the plurality of subtypes, conducting an immune cell infiltration evaluation on the plurality of subtypes, and dividing the plurality of subtypes into a plurality of subtype classes according to results of the enrichment analysis and the immune cell infiltration evaluation;

a comparison step: comparing treatment response rates of different subtype classes through the comparison set to determine a subtype class to be identified;

a classifier construction step: constructing a support vector machine model with feature genes selected from the marker genes and an optimal parameter combination for a support vector machine, wherein the support vector machine model is configured to identify an immune homeostasis like (IHL) class within an immune-related disease data;

a classification step: inputting the immune-related disease data to be classified into the support vector machine model and determining that the immune-related disease data to be classified is of the IHL class; and a treatment step: treating an immune-related disease identified as being of the IHL class based on the classification step with a biological agent therapy of ustekinumab;

wherein the immune-related disease microarray dataset is acquired from the gene expression omnibus (GEO) database, and the immune-related disease microarray dataset comprises an ulcerative colitis (UC) microarray dataset or a Crohn's disease (CD) microarray dataset;

wherein the immune homeostasis like (IHL) class is a subtype class determined based on immune infiltration evaluation results, in which the immune cell infiltration evaluation comprises single-sample gene set enrichment analysis (ssGSEA), and ssGSEA-based immune cell enrichment scores of the IHL class are lower than corresponding ssGSEA-based immune cell enrichment scores of each other subtype class identified in the molecular typing step.

2. The method of molecular typing and subtyping classifications for immune-related diseases according to claim 1, wherein the clustering algorithm is a CrossICC algorithm that is an interactive consensus clustering framework for cross-platform data analysis, the enrichment analysis is performed using a clusterProfiler software package, and the immune cell infiltration evaluation is performed using cell-type identification by estimating relative subsets of ribonucleic acid transcripts (CIBERSORT) and single-sample gene set enrichment analysis (ssGSEA); and the plurality of subtype classes comprise an innate immune activation (IIA) class, a whole immune activation (WIA) class, and an immune homeostasis like (IHL) class, or an IHL class, an IIA class, and an intermediate class.

3. The method of molecular typing and subtyping classifications for immune-related diseases according to claim 1, wherein a method for selecting the feature genes comprises:

setting a maximum number of runs and a number of trees for the marker gene of each of the plurality of subtypes by a random forest method, and inputting marker genes left after screening into Lasso regression of 10-fold cross-validation to leave marker genes with non-zero parameters as the feature genes.

4. The method of molecular typing and subtyping classifications for immune-related diseases according to claim 1, further comprising: conducting a prediction and an evaluation with a constructed support vector machine model in the training set and the validation set, and evaluating performance of classifying by a confusion matrix, wherein:

an accuracy=samples correctly classified/total samples;

a sensitivity=a number of positive samples correctly classified/a total number of positive samples;

a specificity=a number of negative samples correctly classified/a total number of negative samples;

a false positive rate=negative samples determined to be positive/the total number of negative samples; and a false negative rate=positive samples determined to be negative/the total number of positive samples.

5. The method of molecular typing and subtyping classifications for immune-related diseases according to claim 1, wherein a gamma value and a cost value are selected based on the feature genes to obtain the optimal parameter combination.

* * * * *